United States Patent
Ju et al.

(10) Patent No.: US 10,662,463 B2
(45) Date of Patent: May 26, 2020

(54) POLYMER TAGGED NUCLEOTIDES FOR SINGLE MOLECULE ELECTRONIC SNP ASSAY

(71) Applicants: Jingyue Ju, Englewood Cliffs, NJ (US); Youngjin Cho, New York, NY (US); Shiv Kumar, Belle Mead, NJ (US); Sergey Kalachikov, New York, NY (US); Chuanjuan Tao, New York, NY (US); Minchen Chien, Tenafly, NJ (US); James J. Russo, New York, NY (US)

(72) Inventors: Jingyue Ju, Englewood Cliffs, NJ (US); Youngjin Cho, New York, NY (US); Shiv Kumar, Belle Mead, NJ (US); Sergey Kalachikov, New York, NY (US); Chuanjuan Tao, New York, NY (US); Minchen Chien, Tenafly, NJ (US); James J. Russo, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 15/560,820

(22) PCT Filed: Mar. 22, 2016

(86) PCT No.: PCT/US2016/023607
§ 371 (c)(1),
(2) Date: Sep. 22, 2017

(87) PCT Pub. No.: WO2016/154215
PCT Pub. Date: Sep. 29, 2016

(65) Prior Publication Data
US 2018/0112257 A1  Apr. 26, 2018

Related U.S. Application Data

(60) Provisional application No. 62/137,014, filed on Mar. 23, 2015.

(51) Int. Cl.
*C12Q 1/6827* (2018.01)
*C12Q 1/6869* (2018.01)
*G01N 33/487* (2006.01)

(52) U.S. Cl.
CPC ......... *C12Q 1/6827* (2013.01); *C12Q 1/6869* (2013.01); *G01N 33/48721* (2013.01); *C12Q 2565/631* (2013.01)

(58) Field of Classification Search
CPC ............... C12Q 1/6827; C12Q 1/6869; C12Q 2565/631; G01N 33/48721
See application file for complete search history.

(56) References Cited

U.S. PATENT DOCUMENTS

2009/0286245 A1  11/2009  Bjornson et al.
2010/0029494 A1*  2/2010  Cherkasov ............. C07H 19/06
                                                      506/9

(Continued)

FOREIGN PATENT DOCUMENTS

WO  WO 2013/154999 A2  10/2013
WO  WO-2013191793 A1 *  12/2013  ........... C12Q 1/6869

OTHER PUBLICATIONS

Walker, et al, "Key residues for membrane binding, oligomerization, and pore forming activity of staphylococcal alpha-hemolysin identified by cysteine scanning mutagenesis and targeted chemical modification", J Biol Chem, Sep. 29, 1995, vol. 270, No. 39, pp. 23065-23071.

(Continued)

*Primary Examiner* — Joseph G. Dauner
(74) *Attorney, Agent, or Firm* — John P. White; Gary J. Gershik; Cooper & Dunham LLP

(57) ABSTRACT

This invention provides methods of using labeled nucleotide polyphosphate analogues to detect the identity or presence of a nucleotide at certain positions in nucleic acid sequences with single molecule sensitivity using nanopore detection, nucleotides and primer-conjugated nanopore proteins for use in such methods, and processes for producing such nucleotides and primer-conjugated nanopore proteins.

18 Claims, 12 Drawing Sheets

Specification includes a Sequence Listing.

(56) References Cited

U.S. PATENT DOCUMENTS

| | | | |
|---|---|---|---|
| 2010/0093992 A1 | 4/2010 | Cherkasov et al. | |
| 2010/0304381 A1 | 12/2010 | Taing et al. | |
| 2010/0330570 A1* | 12/2010 | Vander Horn | C12Q 1/6827 |
| | | | 435/6.11 |
| 2015/0111759 A1* | 4/2015 | Ju | C12Q 1/42 |
| | | | 506/2 |
| 2015/0119259 A1* | 4/2015 | Ju | C12Q 1/6869 |
| | | | 506/2 |

OTHER PUBLICATIONS

Clarke, et al, "Continuous base identification for single-molecule nanopore DNA sequencing", Nat Nanotechnol, Feb. 22, 2009, vol. 4, No. 4, pp. 265-270.

International Search Report issued in connection with PCT International Application No. PCT/US2016/023607.

Written Opinion of the International Searching Authority issued in connection with PCT International Application No. PCT/US2016/023607.

* cited by examiner

A) Synthesis of ddG4P-Heptyl-NH₂ (Product A)

B) Synthesis of Coumarin-PEG$_n$-NHS Ester (Product B)

C) Coupling of product A and B to yield Coumarin-PEG$_n$-ddG4P

R & R'= H, OH, O-alkyl, Cl, F, $N_3$, $NH_2$, O-allyl, $O-NH_2$ etc
TAG= Nanopore detectable Tag, such as Oligonucleotides, Peptides, PEGs or other polymers Synthetic Scheme for Nanopore Detectable TAG-Nucleotides ddCTP-Cy3-T₂-dSp₈-T₂₀-C3        ddUTP-Cy3-T₁-dSp₃-T₂₃-C3

POLYMER TAGGED NUCLEOTIDES FOR SINGLE MOLECULE ELECTRONIC SNP ASSAY

CROSS-REFERENCE TO RELATED APPLICATIONS

This application is a § 371 national stage of PCT International Application No. PCT/US2016/023607, filed Mar. 22, 2016, claiming the benefit of U.S. Provisional Application No. 62/137,014, filed Mar. 23, 2015, the contents of each of which are hereby incorporated by reference into the application.

Throughout this application, various publications and patents are referenced. Full citations for these references may be found at the end of the specification immediately preceding the claims. The disclosures of these publications and patents in their entirety are hereby incorporated by reference into this application to more fully describe the state of the art to which this invention pertains.

This application incorporates-by-reference nucleotide and/or amino acid sequences which are present in the file named "190725 87413-A-PCT-US Substitute Sequence Listing RBR.txt" which is 2 kilobytes in size, and which was created Jul. 25, 2019 in the IBM-PCT machine format, having an operating system compatibility with MS-Windows, which is contained in the text file filed Jul. 25, 2019 as part of this application.

BACKGROUND OF THE INVENTION

A single nucleotide polymorphism (SNP) is a single base variation in the genome of a living organism. SNPs may occur in coding sequences of genes and non-coding regions of genes, including regulatory regions. SNPs in the coding sequences of the genome are classified as two types: synonymous and nonsynonymous. Synonymous SNPs do not alter the protein sequence due to the degeneracy of the genetic code, while nonsynonymous SNPs change the amino acid sequence of the encoded protein. The nonsynonymous SNPs are further divided into two types: missense and nonsense. A missense mutation is a single nucleotide point mutation leading to a codon that codes for a different amino acid compared to the wild-type, whereas a nonsense mutation is a point mutation that results in a premature stop codon. SNPs that are not in protein-coding regions can impact the function of the genes by altering splicing sequences and binding activity of transcription factors as well as gene expression. Among all the genetic variations, SNPs are the most common genetic differences between human beings. Over 3.1 million SNPs have been characterized from the human genome in a second-generation human haplotype map (Frazer et al. 2007). Thus, SNPs are important biomarkers for investigating the molecular basis underlying the mechanism for disease development, laying a foundation for precision medicine.

The Human Genome Project and the construction of a comprehensive human genome sequence map (Lander et al. 2001, Venter et al. 2001, and Wheeler et al. 2008) provide valuable resources for the study of genetic variations. These genetic differences include SNPs, gene copy number variations, insertions and deletions. SNPs have been established as unique biomarkers for the discovery and characterization disease genes (Kwok 2000 and Roses 2000). These research efforts require the characterization of large number of SNPs with technologies that are cost-effective and high-throughput with high-accuracy. The following DNA sequencing platforms are widely used for characterizing genetic variations: (1) 4-color fluorescent Sanger method (Smith et al. 1986, Ju et al. 1995, Ju et al. 1996, Salas-Solano et al. 1998, and Kheterpal et al. 1996), (2) sequencing by synthesis (SBS) using cleavable fluorescent nucleotide reversible terminators (Ju et al. 2006 and Bentley et al. 2008), (3) SBS with detection of the chemiluminescent signals caused by a cascade of enzymatic reactions following the release of pyrophosphate during polymerase reaction (pyrosequencing) (Margulies et al. 2005), (4) SBS with electronic detection of the released proton during polymerase reaction (ion torrent sequencing) (Rothberg et al. 2011), and (5) single molecule fluorescent SBS methods (Harris et al. 2008 and Eid et al. 2009). However, these sequencing technologies are not designed for pinpoint detection of SNPs, and are still too costly for performing large scale SNP studies. Matrix assisted laser desorption/ionization time-of-flight mass spectrometry (MALDI-TOF MS) and fluorescence emission are two dominant detection methods for SNP analysis. SNP assay approaches using the above two detection methods are reviewed below.

SNP Analysis by MALDI-TOP MS Detection

MALDI-TOF MS measures the mass of the target molecules with highly accurate results in a digital format. It has been used for SNP detection by single base extension (SBE) (Haff et al. 1997, Tang et al. 1999, Ross et al. 1998, Fei et al. 1998, and Griffin et al. 2000), hybridization (Stoerker et al. 2000 and Ross et al. 1997), and invasive cleavage (Griffin et al. 1999 and Lyamichev et al. 1999). MALDI-TOF MS has also been used for gene expression analysis and single-copy DNA haplotyping in the context of nucleotide extension by polymerase (Ding et al., PNAS 100:3059-3064, 2003 and Ding et al., PNAS 100:7449-7453 2003).

Most multiplex SNP analyses make use of the specificity of the SBE reaction catalyzed by polymerase. One of the widely used SNP characterization method utilizes SBE and MALDI-TOF MS detection. In this approach, oligonucleotide primers are designed and synthesized based on the genetic variation in the target gene. The 3'-end of the primer anneals immediately next to a SNP site of the DNA template. A single dideoxynucleotide that is complementary to the SNP site is then incorporated into the primer by DNA polymerase. The identity of the SNP is determined by the mass of the resulting primer extension product obtained from the MALDI-TOF MS spectrum.

SNP Analysis by Fluorescence Detection

Numerous SNP genotyping methods have been developed using fluorescence labeling and detection, including microarray (Hartmann et al. 2009), PCR-RFLP analysis (Chowdhury et al. 2007), and TaqMan real-time genotyping (Bai et al. 2004). There are several advantages to using fluorescence labeling and detection, which include a variety of robust chemical coupling methods to tag the target molecules, high detection sensitivity of several photophysical parameters (fluorescence life time, emission and polarization) and the capability of multiplexing. The molecular inversion probe (MIP) approach has been developed for SNP detection (Hardenbol et al. 2003). In this method, successive extension and ligation of locus-specific DNA probes yields a circular shape at polymorphic sites of the target gene. The linear probes are then selectively degraded, whereas the circular DNA probes that contain allelic information are amplified and analyzed using a microarray with fluorescence detection. Using this approach, Hardenbol et al. (2003) performed genotyping of more than 1,000 SNPs per assay. The MIP method has the advantage of a very high level of multiplexing. However, many enzymatic reaction steps and complicated probe design are required for MIP.

Prior multiplex SNP assays primarily used either mass spectrometric detection or fluorescent tags and optical detection. None of these previous assays offer single molecule detection sensitivity and all require bulky instruments. None used nanopores to identify molecular or polymer tags corresponding to nucleotides of interest or SNPs, so as to identify the nucleotides of interest or SNPs.

SUMMARY OF THE INVENTION

The present invention is directed to a method for identifying a single nucleotide residue of interest at a position within a stretch of consecutive nucleotide residues in a nucleic acid, comprising the steps of:
  (a) incubating the nucleic acid, under an applied voltage, with
    (1) a nanopore;
    (2) an oligonucleotide primer conjugated to the nanopore and hybridized to the nucleotides in the nucleic acid immediately 3' to the single nucleotide residue of interest;
    (3) at least one labeled terminating nucleotide polyphosphate (NPP) analogue, wherein the label is attached to either the base or the terminal phosphate of the NPP analogue; and
    (4) a nucleic acid polymerase;
    so that a NPP analogue is incorporated into the primer if it is complementary to the single nucleotide residue of interest, and the label attached to the incorporated NPP analogue is drawn into the nanopore;
  (b) detecting by nanopore the signature of the label of the NPP analogue incorporated into the primer, so as to identify the incorporated NPP analogue;
  thereby identifying the single nucleotide residue of interest.

The invention is further directed to a method for identifying a single nucleotide residue of interest at a position within a stretch of consecutive nucleotide residues in a nucleic acid, comprising the steps of:
  (a) incubating the nucleic acid, under an applied voltage, with
    (1) a nanopore;
    (2) an oligonucleotide primer conjugated to the nanopore and hybridized to the nucleotides in the nucleic acid immediately 3' to the single nucleotide of interest;
    (3) at least one labeled nucleotide polyphosphate (NPP) analogue, wherein the label is attached to either the base or the terminal phosphate of the NPP analogue;
    (4) a nucleic acid polymerase; and
    (5) a non-catalytic compound which permits transient binding of a complementary NPP analogue to the nucleic acid polymerase and the primed template but inhibits incorporation of the bound NPP analogue;
    so that a NPP analogue is transiently bound to the nucleic acid polymerase and the primed template if the NPP is complementary to the single nucleotide of interest, and the label attached to the transiently bound NPP analogue is drawn into the nanopore;
  (b) detecting by nanopore the signature of the label of the NPP analogue transiently bound to the polymerase and the primed template, so as to identify the NPP analogue;
  thereby identifying the single nucleotide residue of interest.

The invention also provides for an assay for performing any of the methods of the invention.

The invention also provides for a dideoxynucleotide polyphosphate (ddNPP) analogue, comprising a label attached to the terminal phosphate thereof, where the polyphosphate comprises 3-10 phosphate units.

The invention also provides for a deoxynucleotide polyphosphate (dNPP) analogue, comprising a label attached to the terminal phosphate thereof, where the polyphosphate comprises 3-10 phosphate units.

The invention also provides for a ribonucleotide polyphosphate (rNPP) analogue, comprising a label attached to the terminal phosphate thereof, where the polyphosphate comprises 3-10 phosphate units.

The invention also provides for a dideoxynucleotide tetraphosphate (ddN4P) analogue, comprising a coumarin-polyethylene glycol (PEG)-aminopropargyl label attached to the terminal phosphate thereof.

The invention also provides for a composition comprising four ddN4P analogues of the invention, wherein each ddN4P comprises a different base and a distinct label formed by a polymer, each with a different number (n) of monomers.

The invention also provides for a process for producing a ddN4P analogue of the invention, comprising:
  a) contacting a ddN4P with diaminoheptane in carbodiimide (EDAC) and imidazole buffer under conditions permitting the diaminoheptane to attach to the terminal phosphate;
  b) contacting a 6-methoxycoumarin N-hydroxysuccinimidyl ester (NHS) with an amino-$PEG_n$-acid moiety in dimethylformamide, wherein n is the number of ethylene glycol monomers in the PEG, under conditions permitting the production of a coumarin-$PEG_n$-acid compound;
  c) reacting the product of step b) with N,N-disuccinimidyl carbonate in dimethylformamide, under conditions permitting the production of a coumarin-$PEG_n$-NHS compound; and
  d) reacting the products of steps a) and c) to produce a coumarin-$PEG_n$-ddN4P analogue.

The invention also provides for a process for producing the ddG4P analogue of the invention, comprising:
  a) contacting a ddG4P with diaminoheptane in carbodiimide (EDAC) and imidazole buffer under conditions permitting the diaminoheptane to attach to the terminal phosphate;
  b) contacting a 6-methoxycoumarin N-hydroxysuccinimidyl ester (NHS) with an amino-PEG-acid moiety in dimethylformamide, wherein n is the number of ethylene glycol monomers in the PEG, under conditions permitting the production of a coumarin-PEG-acid compound;
  c) reacting the product of step b) with N,N disuccinimidyl carbonate in dimethylformamide, under conditions permitting the production of a coumarin-PEG-NHS compound; and
  d) reacting the products of steps a) and c) to produce a coumarin-$PEG_n$-ddG4P analogue.

The invention also provides for a dideoxynucleotide triphosphate (ddNTP) analogue, comprising a coumarin-polyethylene glycol (PEG)-aminopropargyl label attached to the base thereof.

The invention also provides for a composition comprising four ddNTP analogues of the invention, wherein each ddNTP comprises a different base and a distinct label formed by a polymer, each with a different number (n) of monomers.

The invention also provides for a dideoxynucleotide polyphosphate (ddNPP) analogue, comprising a label attached to the base thereof, where the polyphosphate comprises 3-10 phosphate units.

The invention also provides for a deoxynucleotide polyphosphate (dNPP) analogue, comprising a label attached to the base thereof, where the polyphosphate comprises 3-10 phosphate units.

The invention also provides for a ribonucleotide polyphosphate (rNPP) analogue, comprising a label attached to the base thereof, where the polyphosphate comprises 3-10 phosphate units.

The invention also provides for a process for producing a ddNTP analogue of the invention, comprising:
  a) contacting a 6-methoxycoumarin N-hydroxysuccinimidyl ester (NHS) with an amino-$PEG_n$-acid moiety in dimethylformamide, wherein n is the number of ethylene glycol monomers in the PEG, under conditions permitting the production of a coumarin-$PEG_n$-acid compound;
  b) reacting the product of step a) with N,N-disuccinimidyl carbonate in dimethylformamide, under conditions permitting the production of a coumarin-$PEG_n$-NHS compound; and
  c) reacting the product of step b) with an aminopropargyl-ddNTP, wherein the aminopropargyl moiety is base-attached, in dimethylformamide, to produce a coumarin-$PEG_n$-aminopropargyl-ddNTP.

The invention also provides for a process for producing a polymer tagged ddNTP analogue, comprising:
  a) contacting a 5(7)-propargylamino-ddNTP with amino-protected caproic acid NHS ester;
  b) reacting the product of step a) with ammonium hydroxide to produce 5(7)-propargylamidoaminocaproyl-ddNTPs;
  c) reacting the product of step b) with azidobutyric acid NHS ester; and
  d) reacting the product of step c) with 5'-alkynyl-oligonucleotide tag to produce oligonucleotide tagged ddNTPs.

In some cases the label or tag attached to the base moiety of the nucleoside polyphosphate can be an oligonucleotide or peptide. The oligonucleotide can be of any length from 10-100 monomeric units of thymidine, cytidine, adenosine, guanosine, or derivatives thereof, abasic units (deoxyribose units), and non-hydrogen bond forming modified base units.

The oligonucleotide may consists of phosphodiester linkage, phosphorothioate linkage, borano-phosphate, and methyl phosphonate linkage between the two monomeric units. The examples of oligonucleotide-tags have been disclosed in an earlier published patent application "Chemical methods for producing tagged nucleotides" US 2015/0368710 which is incorporated herein as a reference.

Connection of the nucleotides to the tag can also be achieved by the formation of a disulfide, formation of an amide, formation of an ester, by alkylation (e.g., using a substituted iodoacetamide reagent) or forming adducts using aldehydes and amines or hydrazines, azide-alkyn coupling or tetrazine-diene coupling. Numerous conjugation chemistries can be found in Bioconjugate Techniques by Greg T. Hermanson, (2008), which is incorporated herein by reference in its entirety.

Specific examples of reactive groups on the nucleotides or the Oligonucleotide Tags and groups with which groups can react are provided in Table 1. These reactive groups with which they can react can be present either on the linker or on the tag

TABLE 1

Possible Reactive Substituent and Functional Groups Reactive Therewith

| Reactive Groups | Functional Groups |
|---|---|
| Succinimidyl esters | Primary amino, secondary amino |
| Anhydrides, acid halides | Amino and Hydroxyl groups |
| Carboxyl | Amino, Hydroxy, Thiols |
| Aldehyde, Isothiocyanate & Isocyanates | Amino groups |
| Vinyl sulphone & Dichlorotriazine | Amino groups |
| Haloacetamides | Thiols, Imidazoles |
| Maleimides | Thiols, Hydroxy, Amino |
| Thiols | Thiols, Maleimide, Haloacetamide |
| Phosphoramidites, Activated Phosphates | Hydroxy, Amino, Thiol groups |
| Azide | Alkyne |
| Tetrazine | Dienes |

The invention also provides for an alpha hemolysin protein, having a primer conjugated thereto.

The invention also provides for a process for producing the primer-conjugated α-hemolysin of the invention, comprising:
  a) contacting a sulfosuccinimidyl-4-(N-maleimidomethyl) cyclohexane-1-carboxylate (sSMCC) hetero bifunctional crosslinker, comprising an amido-reactive N-hydroxysuccinimide (NHS) ester and a thiol-reactive maleimide group at opposite ends, with a primer comprising a terminal amino group, under conditions permitting the terminal amino group to react with the amido-reactive NHS ester;
  b) removing residual unreacted sSMCCs from the solution; and
  c) contacting the product resulting from step a) with an α-hemolysin, wherein the α-hemolysin comprises a cysteine mutation at position 46, under conditions permitting the thiol-reactive maleimide group to react with the cysteine residue at position 46;
thereby conjugating the primer to the α-hemolysin.

The invention also provides for a conductance measurement system comprising:
  a) an electrically resistive barrier separating at least a first and a second electrolyte solution;
    said electrically resistive barrier comprises at least one pore with a diameter on nanometer scale;
    said at least one pore being configured to allow an ionic current to be driven across said first and second electrolyte solutions by an applied potential;
  b) at least one labeled terminating nucleotide polyphosphate (NPP) analogue, wherein the label is attached to either the base or the terminal phosphate of the NPP analogue, in at least one of said first and second electrolyte solutions; and
  c) a means of measuring the ionic current and a means of recording its time course as a time series, including time periods when at least one pore is unobstructed by the label and also time periods when a label causes pulses of reduced conductance.

(SEQ ID No: 2)
MADSDINIKTGTTDIGSNTTVKTGDLVTYDKENGMHKKVFYSFIDDCNHN

KKLLVIRTKGTIAGQYRVYSEEGANKSGLAWPSAFKVQLQLPDNEVAQIS

DYYPRNSIDTKEYMSTLTYGFNGNVTGDDTGKIGGLIGANVSIGHTLKYV

QPDFKTILESPTDKKVGWKVIFNNMVNQNWGPYDRDSWNPVYGNQLFMKT

RNGSMKAAENFLDPNKASSLLSSGFSPDFATVITMDRKASKQQTNIDVIY

ERVRDDYQLHWTSTNWKGTNTKDKTWDRSSERYKIDWEKEEMTNKGHHHH

HH.

Figure 12:
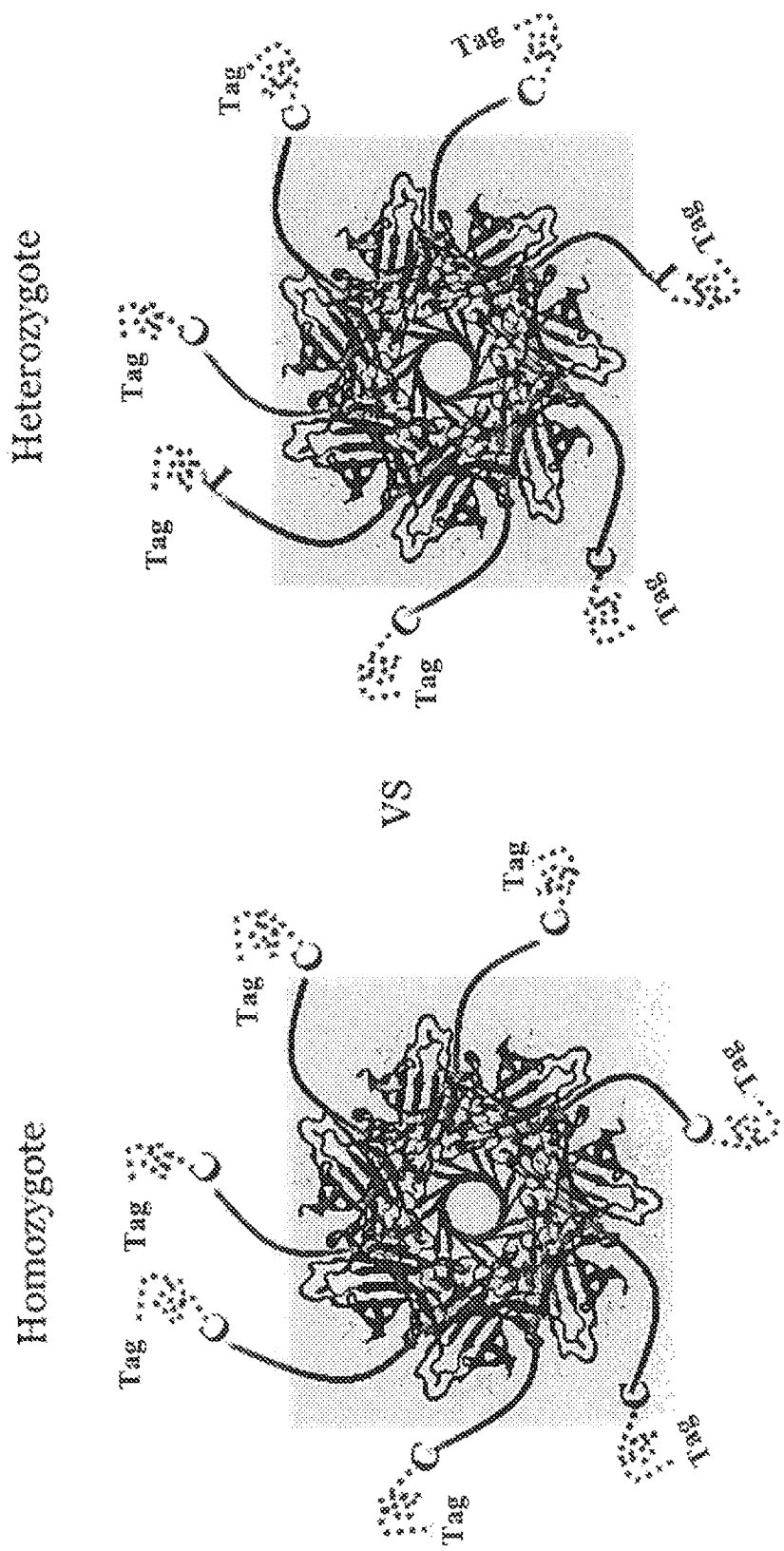

FIG. 12. Two possible scenarios after the extension reaction. The left figure shows an example of a homozygous genotype where the SNP primers are all extended by the same nucleotide representing the two identical alleles. The right figure indicates the case for a heterozygous genotype where each primer is extended by one of two different nucleotides each carrying a unique tag representing the two different alleles.

DETAILED DESCRIPTION OF THE INVENTION

While various embodiments of the invention have been shown and described herein, it will be obvious to those skilled in the art that such embodiments are provided by way of example only. Numerous variations, changes, and substitutes may occur to those skilled in the art without departing from the invention. It should be understood that various alternatives to the embodiments of the invention described herein may be employed.

Terms

As used herein, and unless stated otherwise, each of the following terms shall have the definition set forth below.

| | |
|---|---|
| A | Adenine; |
| C | Cytosine; |
| DNA | Deoxyribonucleic acid; |
| G | Guanine; |
| RNA | Ribonucleic acid; |
| T | Thymine; and |
| U | Uracil |

The articles "a", "an" and "the" are non-limiting. For example, "the method" includes the broadest definition of the meaning of the phrase, which can be more than one method.

"Signature" of a compound in a pore shall include, for example, a signal or change occurring when the compound passes through, resides in, or otherwise interacts with the pore. One such change may be an electronic signature.

"Electronic signature" of a nucleotide or other molecules, such as labels and polymer tags captured by the pore or passing through a pore via application of an electric field shall include, for example, the duration of the nucleotide's or molecule's capture by or passage through the pore together with the observed amplitude of current during that passage. Electronic signatures can be visualized, for example, by a plot of current (e.g. pA) versus time. Electronic signature for a DNA is also envisioned and can be, for example, a plot of current (e.g. pA) versus time for the DNA to be captured by or pass through the pore via application of an electric field.

"Nanopore" includes, for example, a structure comprising (a) a first and a second compartment separated by a physical barrier, which barrier has at least one pore with a diameter, for example, of from about 1 to 10 nm, and (b) a means for applying an electric field across the barrier so that a charged molecule such as DNA, nucleotide, nucleotide analogue, or tag can be captured by the pore or pass from the first compartment through the pore to the second compartment. The nanopore ideally further comprises a means for measuring the electronic signature of a molecule captured by the pore or passing through its barrier. The nanopore barrier may be synthetic or naturally occurring, or both, in part. Barriers can, for example, be biological, comprising naturally-occurring compounds or materials derived from such compounds. This includes, for example, lipid bilayers having therein α-hemolysin, oligomeric protein channels such as porins, and synthetic peptides and the like. Barriers can also be, for example, solid state nanopores including, for example, inorganic plates having one or more holes of a suitable size. Herein "nanopore", "nanopore barrier" and the "pore" in the nanopore barrier are sometimes used equivalently.

"Detection via nanopore" or "detection by a nanopore" includes, for example, detecting a change in ionic current through a nanopore caused by a molecule captured by the pore or entering, translocating through, or otherwise interacting with a nanopore. For example, in an aqueous ionic salt solution such as KCl, when an appropriate voltage is applied across the membrane, the pore formed by an α-hemolysin channel conducts a sufficiently strong and steady ionic current. A charged molecule can then be driven through the pore by the applied electric field, thus blocking or reducing the ionic current that would be otherwise unimpeded. This process of passage generates an electronic signature. A particular molecule, when captured by the pore or entering and passing through the nanopore, generates a characteristic signature that distinguishes it from other molecules. The duration of the blockade and the signal strength is related to the steric, electronic, and other physical and chemical properties of the molecule. Thus a specific event diagram, which is a plot of translocation time versus blockade current, is obtained and used to identify the molecule by single channel recording techniques based on characteristic parameters such as translocation current, translocation duration, and their corresponding dispersion in the diagram.

"Nucleic acid" shall mean any nucleic acid molecule, including, without limitation, DNA, RNA and hybrids thereof as well as their analogues. The nucleic acid bases that form nucleic acid molecules can be the bases A, C, G, T and U, as well as derivatives thereof. Derivatives of these bases are well known in the art, and are exemplified in PCR Systems, Reagents and Consumables (Perkin Elmer Catalogue 1996-1997, Roche Molecular Systems, Inc., Branchburg, N.J., USA).

"Hybridize" shall mean the annealing of one single-stranded nucleic acid (such as primer) to another nucleic acid based on the well-understood principle of sequence complementarity. In an embodiment the other nucleic acid is a single-stranded nucleic acid. The propensity for hybridization between nucleic acids depends on the temperature and ionic strength of their miliu, the length of the nucleic acids and the degree of complementarity. The effect of these parameters on hybridization is described in, for example, Sambrook J, Fritsch E F, Maniatis T., Molecular cloning: a laboratory manual, Cold Spring Harbor Laboratory Press, New York (1989). As used herein, hybridization of a primer, or of a DNA extension product, respectively, is extendable by creation of a phosphodiester bond with an available nucleotide or nucleotide analogue capable of forming a phosphodiester bond, therewith.

"Primer" as used herein (a primer sequence) is a short, usually chemically synthesized oligonucleotide, of appropriate length, for example about 10-30 bases, sufficient to hybridize to a target DNA (e.g. a single stranded DNA) and permit the addition of a nucleotide residue thereto, or oligonucleotide or polynucleotide synthesis therefrom, under suitable conditions well-known in the art. In an embodiment the primer is a DNA primer, i.e. a primer consisting of, or largely consisting of, deoxyribonucleotide residues or their analogues. The primers are designed to have a sequence that is the complement of a region of template/target DNA to which the primer hybridizes. The addition of a nucleotide residue to the 3' end of a primer by formation of a phosphodiester bond results in a DNA extension product. The addition of a nucleotide residue to the 3' end of the DNA extension product by formation of a phosphodiester bond results in a further DNA extension product.

"Nucleotide," as used herein, refers to a nucleoside-5'-polyphosphate compound, or a structural analog thereof, which can be incorporated by a nucleic acid polymerase to extend a growing nucleic acid chain (such as a primer). Nucleotides may comprise bases such as A, C, G, T, U, or analogues thereof, and may comprise 3, 4, 5, 6, 7, 8, or more phosphates in the phosphate group. Nucleotides may be modified at one or more of the base, sugar, or phosphate group. A nucleotide may have a label or tag attached (a "tagged nucleotide" or "labeled nucleotide").

"Terminating nucleotide" shall mean any modified or unmodified nucleotide which, when incorporated into a nucleotide strand, prevents or severely hampers further elongation of the nucleotide strand. One example is a dideoxynucleotide. "Terminating nucleotide" also comprises any nucleotide which will form a ternary complex with the primed template and DNA polymerase in the presence of non-catalytic metal ions preventing incorporation of the nucleotide (Vander Horn et al, 2014). A terminating nucleotide may have a label or tag attached.

"Polymer", as used herein, refers to any molecule or moiety comprised of a plurality of repeating units. This includes both homopolymers, polymers comprised of identical repeating units, such as polyethylene glycol, and heteropolymers, polymers comprised of similar but different repeating units, such as certain oligonucleotides.

"Polymerase," as used herein, refers to any natural or non-naturally occurring enzyme or other catalyst that is capable of catalyzing a polymerization reaction, such as the polymerization of nucleotide monomers to form a nucleic acid polymer. Exemplary polymerases that may be used in the compositions and methods of the present disclosure include the nucleic acid polymerases such as DNA polymerase, DNA- or RNA-dependent RNA polymerase, and reverse transcriptase.

As used herein, "substantially identical" or "substantially fully complementary" sequences have at least about 80% sequence identity or complementarity, respectively, to a nucleotide sequence. Substantially identical sequences or substantially fully complementary sequences may have at least about 85%, 90%, 95% or 100% sequence identity or complementarity, respectively.

Principle of Single Molecule Electronic SNP Assay

The invention disclosed herein pertains to methods of using labeled nucleotide polyphosphate analogues to detect the identity or presence of a nucleotide at certain positions in DNA (or RNA, mutatis mutandis) sequences with single molecule sensitivity using nanopore detection, nucleotides and primer-conjugated nanopore proteins for use in such methods, and processes for producing such nucleotides and primer-conjugated nanopore proteins.

Figure 1:
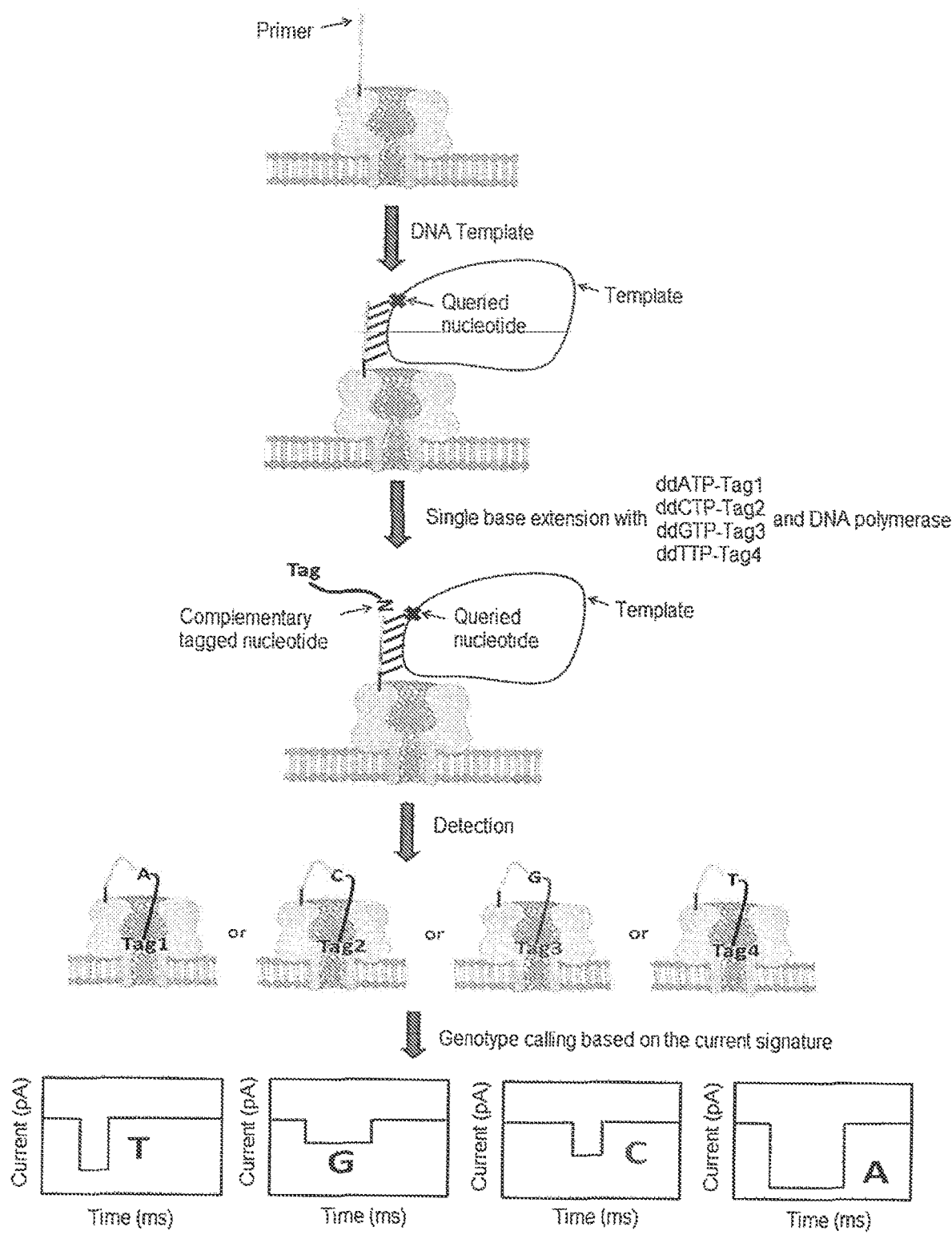
FIG. 1. Exemplary scheme of single molecule electronic SNP genotyping using polymer-labeled ddNTPs (in this example, the tags are attached to the base of the ddNTPs) in a primer-conjugated nanopore array. Nanopores that are conjugated with SNP primers (i.e. primers which are substantially fully complementary to the nucleotides in the DNA immediately 3' to the single nucleotide of interest, identified as the queried nucleotide) are prepared. Single base extension is performed by adding 4 differently tagged ddNTPs, DNA polymerase and DNA templates. The primers having complementary sequences to the added templates are extended by the polymerase with tagged ddNTPs. Under an applied voltage, the tags are pulled into the pore and the current signal from the pore is read, revealing the specific genotype of the template.

Four ddNTPs are labeled with different length PEG molecules or other polymer tags, such that each nucleotide can be well discriminated by detecting the tags in a nanopore system after the nucleotides are incorporated into the primer to determine the genotype of the complementary nucleotide of the template. For example, first, four different PEGs with 16, 20, 24 and 36 ethylene glycol units that have been shown to display distinct nanopore blockade signals for potential DNA sequencing by synthesis (Kumar et al. 2012) are selected as tags to label ddNTPs. To avoid interrupting the active sites of DNA polymerase, two positions in ddNTPs are tested for the tag attachment: either the terminal phosphate or the specific position of the base in each nucleotide. Second, in order to perform the analysis, a homogeneous SNP genotyping platform is prepared by conjugating a primer to the cap of alpha hemolysin (αHL). Third, using these unique reagents, the tagged-ddNTPs and primer-conjugated nanopores, single molecule electronic SNP genotyping is performed in the nanopore system. Specifically, primer-conjugated nanopores are reconstituted in the lipid bilayers. After confirming the currents that indicate insertion of the pore, single base extension (SBE) is performed by adding a specific circularized template which has complementary sequences to the primer, DNA polymerase and four differently tagged ddNTPs to the pores. Under an applied voltage, the tags from each extended primer are captured in the pore and the distinct current signatures from each pore are analyzed, decoding the nucleotide incorporated into the extended primer. This, in turn, reveals the genotype of the template (FIG. 1).

Figure 2:
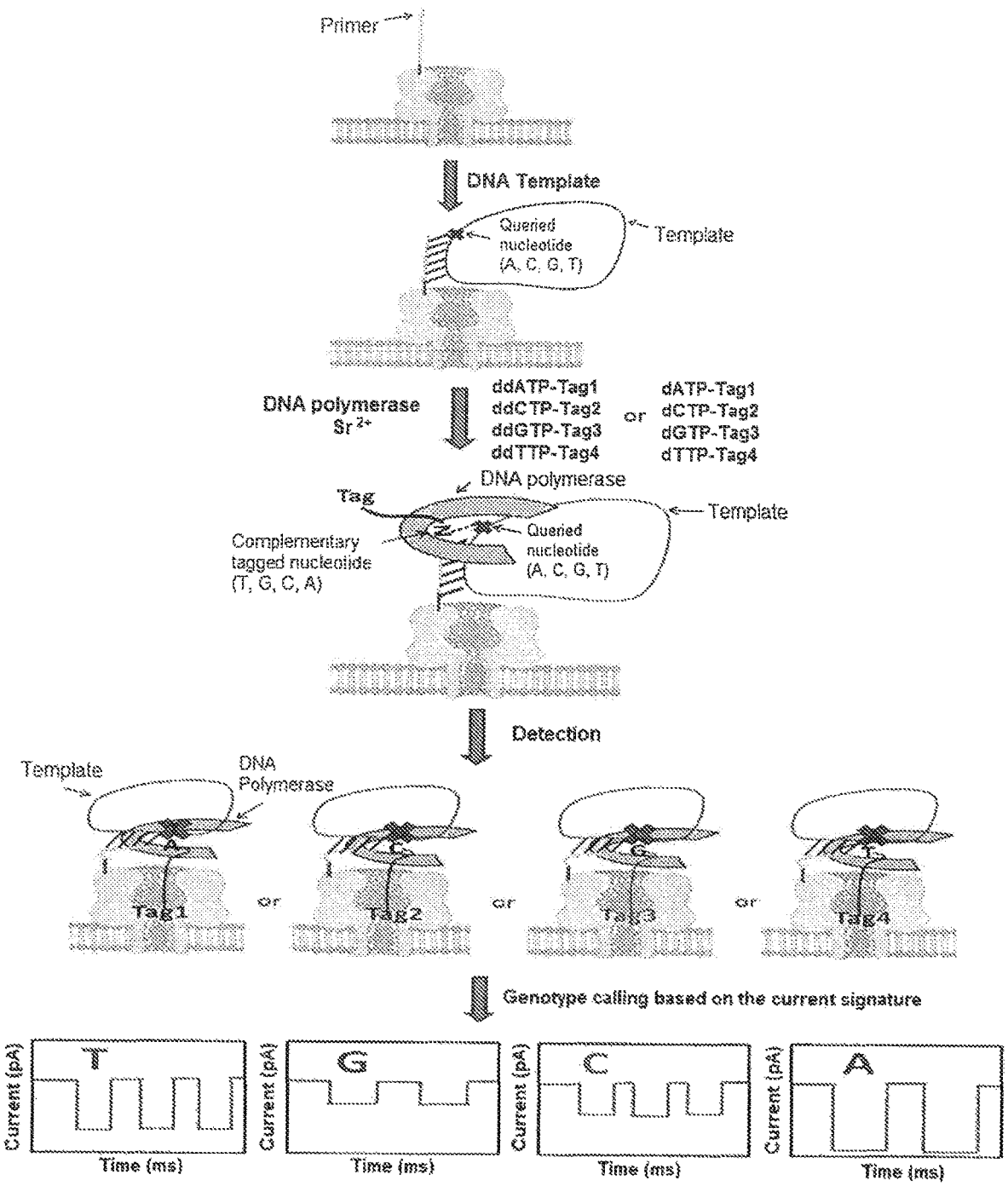
FIG. 2. Exemplary scheme of single molecule electronic SNP genotyping using 4 tagged nucleotides in a primer-conjugated nanopore array in the presence of non-catalytic metal ions such as $Sr^{2+}$ (in this example, the tags can be attached to either the base or the terminal phosphate of the dNTPs or ddNTPs). Nanopores that are conjugated with SNP primers are prepared. The closed ternary complex of DNA polymerase, a matched template-primer pair and the complementary tagged nucleotide to the queried site in the template are formed and the complex is temporarily paused in the presence of non-catalytic $Sr^{2+}$ ion. During this frozen period, the tags on the incoming nucleotide in the ternary complex are pulled into the pore under an applied voltage and the current signal from the pore is read, revealing the specific genotype of the template.
Figure 3:
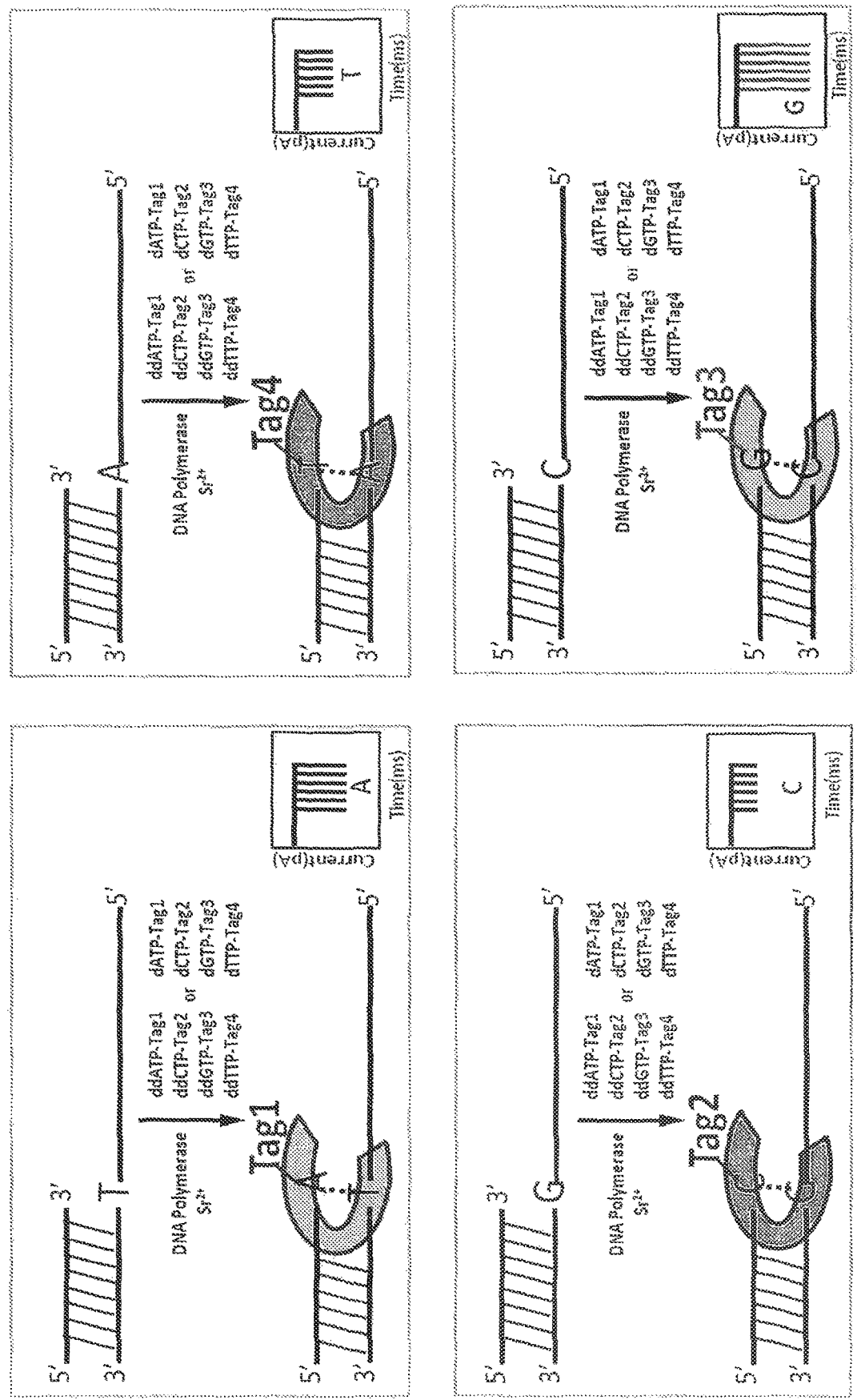
FIG. 3. Single molecule electronic SNP genotyping scheme and the expected current signals by using 4 tagged nucleotides. Four tagged nucleotides are added to the primer-template moiety attached to the nanopore in solution containing non-catalytic $Sr^{2+}$ ion and polymerase such that one of the tag-nucleotides complementary to the next base on the template forms a ternary complex, but is not incorporated, and current blockade signal is recorded multiple times for SNP detection.

Alternatively, the DNA polymerase can be momentarily stalled in the closed ternary complex by adding a high concentration of non-catalytic $Sr^{2+}$ ion which permits transient-binding of a complementary nucleotide and a primed template to DNA polymerase but inhibits the incorporation of the bound nucleotide as described by Vander Horn et al. (2014). Thus, the addition of $Sr^2$ temporally pauses DNA polymerase complex and extend the time span of the nucleotide binding in the closed form of DNA polymerase without the incorporation step. This prolonged time allows the tags to be captured and read in the pore multiple times generating stuttering current blockade signatures. In addition, both tagged dideoxynucleotides and deoxynucleotides can be employed for recognition of the inquired SNP site and are expected to generate the same results since the nucleotide in this approach is not in fact incorporated into the primer but complexed with the polymerase in the ternary complex in the presence of $Sr^{2+}$. Schemes of the alternative assay using $Sr^{2+}$ ion are provided in FIG. 2 and FIG. 3. Overall, the demonstration of these configurations lays a foundation for the development of a complete system for the single molecule electronic SNP genotyping assay.

Embodiments of the Invention

The present invention is directed to a method for identifying a single nucleotide residue of interest at a position within a stretch of consecutive nucleotide residues in a nucleic acid, comprising the steps of:
(a) incubating the nucleic acid, under an applied voltage, with
(1) a nanopore;
(2) an oligonucleotide primer conjugated to the nanopore and hybridized to the nucleotides in the nucleic acid immediately 3' to the single nucleotide residue of interest;
(3) at least one labeled terminating nucleotide polyphosphate (NPP) analogue, wherein the label is attached to either the base or the terminal phosphate of the NPP analogue; and
(4) a nucleic acid polymerase;
so that a NPP analogue is incorporated into the primer if it is complementary to the single nucleotide residue of interest, and the label attached to the incorporated NPP analogue is drawn into the nanopore;
(b) detecting by nanopore the signature of the label of the NPP analogue incorporated into the primer, so as to identify the incorporated NPP analogue;
thereby identifying the single nucleotide residue of interest.

In an embodiment of the invention, in step (a) the nucleic acid is incubated with at least two NPP analogues. In a further embodiment, the nucleic acid is incubated with at least four NPP analogues. In a further embodiment, the nucleic acid is incubated with exactly four NPP analogues.

In an embodiment of the invention, in step (a) the nucleic acid is incubated with one NPP analogue, and if the NPP analogue is not incorporated, iteratively repeating the incubating with a different NPP analogue until a NPP analogue is incorporated.

The invention is further directed to a method for identifying a single nucleotide residue of interest at a position within a stretch of consecutive nucleotide residues in a nucleic acid, comprising the steps of:
a) incubating the nucleic acid, under an applied voltage, with
(1) a nanopore;
(2) an oligonucleotide primer conjugated to the nanopore and hybridized to the nucleotides in the nucleic acid immediately 3' to the single nucleotide of interest;

(3) at least one labeled nucleotide polyphosphate (NPP) analogue, wherein the label is attached to either the base or the terminal phosphate of the NPP analogue;
(4) a nucleic acid polymerase; and
(5) a non-catalytic compound which permits transient binding of a complementary NPP analogue to the nucleic acid polymerase and the primed template but inhibits incorporation of the bound NPP analogue;
so that a NPP analogue is transiently bound to the nucleic acid polymerase and the primed template if the NPP is complementary to the single nucleotide of interest, and the label attached to the transiently bound NPP analogue is drawn into the nanopore;
b) detecting by nanopore the signature of the label of the NPP analogue transiently bound to the polymerase and the primed template, so as to identify the NPP analogue;
thereby identifying the single nucleotide residue of interest.

In an embodiment of the invention, in step (a) the nucleic acid is incubated with at least two NPP analogues. In a further embodiment, the nucleic acid is incubated with at least four NPP analogues. In a further embodiment, the nucleic acid is incubated with exactly four NPP analogues.

In an embodiment of the invention, in step (a) the nucleic acid is incubated with one NPP analogue, and if the NPP analogue does not transiently bind to the nucleic acid polymerase, iteratively repeating the incubating with a different NPP analogue until a NPP analogue is transiently bound.

In an embodiment of the invention, the non-catalytic compound is $Sr^{2+}$.

In an embodiment of the invention, each NPP is a deoxyribonucleotide polyphosphate (dNPP) or its analogue.

In another embodiment of the invention, each NPP is a dideoxyribonucleotide polyphosphate (ddNPP) or its analogue.

In an embodiment of the invention, each ddNPP or its analogue comprises a label having a coumarin-PEG moiety.

In an embodiment of the invention, each ddNPP or its analogue comprises a label having a oligonucleotide-based tag varying from about 10-50 monomeric units.

In an embodiment of the invention, each NPP is a ribonucleotide polyphosphate (rNPP) or its analogue.

In an embodiment of the invention, the nucleic acid is single-stranded DNA. In another embodiment, the nucleic acid is double-stranded DNA. In another embodiment, the nucleic acid is single-stranded RNA. In another embodiment, the nucleic acid is double-stranded RNA.

In an embodiment of the invention, the nucleic acid is single-stranded DNA or double-stranded DNA and the nucleic acid polymerase is DNA polymerase. In another embodiment, the nucleic acid is RNA and the nucleic acid polymerase is reverse transcriptase.

In an embodiment of the invention, the nucleic acid polymerase is RNA polymerase.

In an embodiment of the invention, the label is attached to the base. In another embodiment, the label is attached to the terminal phosphate.

In an embodiment of the invention, the label comprises one or more of ethylene glycol, an amino acid, a carbohydrate, a peptide, a dye, a chemiluminescent compound, a mononucleotide, a dinucleotide, a trinucleotide, a tetranucleotide, a pentanucleotide, a hexanucleotide, an oligonucleotide, an aliphatic acid, an aromatic acid, an alcohol, a thiol group, a cyano group, a nitro group, an alkyl group, an alkenyl group, an alkynyl group, an azido group, or a combination thereof.

In an embodiment of the invention, the label is a polymeric label. In a further embodiment, the labels are polyethylene glycol (PEG) labels. In a further embodiment, the PEG labels each have a different length from each other. In another embodiment, the labels are oligonucleotide labels (Fuller et al 2015).

In an embodiment of the invention, the signature is an electronic signature. In a further embodiment, the electronic signature is an electrical current blockade signature. In a further embodiment, the electrical current blockade signature is a stuttering current blockade signature.

In an embodiment of the invention, the nanopore is a solid-state nanopore. In another embodiment, the nanopore is in a solid state membrane. In another embodiment, the nanopore is a biological pore. In another embodiment, the nanopore is proteinaceous. In another embodiment, the nanopore comprises alpha hemolysin. In another embodiment, each nanopore comprises seven alpha hemolysin monomers, any or all of which are conjugated to an identical primer. In another embodiment, the nanopore comprises MspA (Manrao et al 2012). In another embodiment, each nanopore comprises eight alpha MspA monomers, any or all of which are conjugated to an identical primer. In another embodiment, the nanopore comprises CsgG (Goyal et al 2014). In another embodiment, each nanopore comprises nine alpha CsgG monomers, any or all of which are conjugated to an identical primer.

In an embodiment of the invention, the nucleic acid is incubated with four coumarin-PEG-ddNPPs, each comprising a different base, and each comprising a coumarin-PEG-label of a different length. In a further embodiment, the four coumarin-PEG labels are coumarin-PEG16, coumarin-PEG20, coumarin-PEG24, and coumarin-PEG36. In an embodiment, each coumarin-PEG label is attached to the terminal phosphate of the ddNPP. In another embodiment, each coumarin-PEG label is a coumarin-PEG-aminopropargyl label and is attached to the 5-position of the base if the ddNPP is ddCPP, ddUPP, or ddTPP, and to the 7-position of the base if the ddNPP is ddAPP or ddGPP.

In an embodiment of the invention, the nucleic acid is incubated with four oligonucleotide-tagged ddNPPs, each comprising a different base, and each comprising an oligonucleotide tag of different lengths and compositions. In a further embodiment, the four oligonucleotide tags are as described in Fuller et al (2015). In an embodiment, each oligonucleotide tag is attached to the terminal phosphate of the ddNPP. In another embodiment, each oligonucleotide tag is attached to the 5-position of the base if the ddNPP is ddCPP, ddUPP, or ddTPP, and to the 7-position of the base if the ddNPP is ddAPP or ddGPP.

In an embodiment of the invention the sequence of the primer is 10-40 nucleotides long. In another embodiment, the sequence of the primer is 18-24 nucleotides long.

The invention also provides for an assay for performing any of the methods of the invention.

The invention also provides for a dideoxynucleotide tetraphosphate (ddN4P) analogue, comprising a coumarin-polyethylene glycol (PEG)-aminopropargyl label attached to the terminal phosphate thereof.

In an embodiment of the invention, the ddN4P analogue has the structure

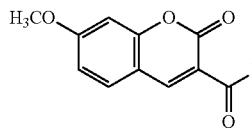

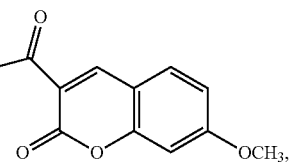

wherein n is 16, 20, 24, or 36, and wherein B is a base selected from the group consisting of adenine, cytosine, thymine, guanine, and uracil.

In an embodiment, the base is guanine.

The invention also provides for a composition comprising four ddN4P analogues of the invention, wherein each ddN4P comprises a different base and a unique polymeric tag, and each tag has a different composition and number of monomers.

In an embodiment of the invention, wherein the four ddN4P analogues are a ddA4P analogue, a ddG4P analogue, a ddC4P analogue, and either a ddT4P analogue or a ddU4P analogue.

The invention also provides for a process for producing a ddN4P analogue of the invention, comprising:

a) contacting a ddN4P with diaminoheptane in carbodiimide (EDAC) and imidazole buffer under conditions permitting the diaminoheptane to attach to the terminal phosphate;
b) contacting a 6-methoxycoumarin N-hydroxysuccinimidyl ester (NHS) with an amino-PEG$_n$-acid moiety in dimethylformamide, wherein n is the number of ethylene glycol monomers in the PEG, under conditions permitting the production of a coumarin-PEG-acid compound;
c) reacting the product of step b) with N,N disuccinimidyl carbonate in dimethylformamide, under conditions permitting the production of a coumarin-PEG$_n$-NHS compound; and
d) reacting the products of steps a) and c) to produce a coumarin-PEG$_n$-ddN4P analogue.

In an embodiment, the process further comprises, prior to step a), reacting a ddNTP with tributylammonium phosphate in order to obtain the ddN4P.

The invention also provides for a process for producing the ddG4P analogue of the invention, comprising:

a) contacting a ddG4P with diaminoheptane in carbodiimide (EDAC) and imidazole buffer under conditions permitting the diaminoheptane to attach to the terminal phosphate;
b) contacting a 6-methoxycoumarin N-hydroxysuccinimidyl ester (NHS) with an amino-PEG$_n$-acid moiety in dimethylformamide, wherein n is the number of ethylene glycol monomers in the PEG, under conditions permitting the production of a coumarin-PEG$_n$-acid compound;
c) reacting the product of step b) with N,N-disuccinimidyl carbonate in dimethylformamide, under conditions permitting the production of a coumarin-PEG$_n$-NHS compound; and
d) reacting the products of steps a) and c) to produce a coumarin-PEG$_n$-ddG4P analogue.

In an embodiment, the process further comprises, prior to step a), reacting a ddGTP with tributylammonium phosphate in order to obtain the ddG4P.

The invention also provides for a dideoxynucleotide triphosphate (ddNTP) analogue, comprising a coumarin-polyethylene glycol (PEG)-aminopropargyl label attached to the base thereof.

In an embodiment, the ddNTP analogue has the structure

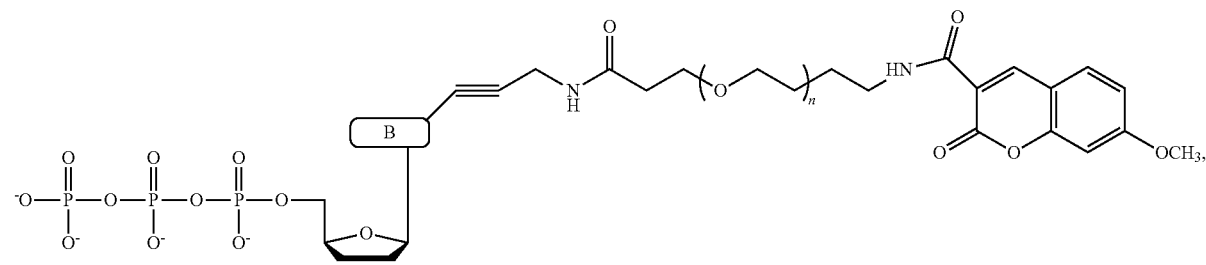

wherein B is a base selected from the group adenine, cytosine, thymine, guanine, and uracil or derivatives thereof; and n is 16, 20, 24, or 36.

The invention also provides for a composition comprising four ddNTP analogues of the invention, wherein each ddNTP comprises a different base and a unique polymeric tag, and each tag has a different composition and number of monomers.

In a further embodiment, the four ddNTP analogues are a ddATP analogue, a ddGTP analogue, a ddCTP analogue, and either a ddTTP analogue or a ddUTP analogue.

The invention also provides for a process for producing a ddNTP analogue of the invention, comprising:

a) contacting a 6-methoxycoumarin N-hydroxysuccinimidyl ester (NHS) with an amino-PEG$_n$-acid moiety in dimethylformamide, wherein n is the number of ethylene glycol monomers in the PEG, under conditions permitting the production of a coumarin-PEG$_n$-acid compound;
b) reacting the product of step a) with N,N disuccinimidyl carbonate in dimethylformamide, under conditions permitting the production of a coumarin-PEG$_n$-NHS compound; and
c) reacting the product of step b) with an aminopropargyl-ddNTP, wherein the aminopropargyl moiety is base-attached, in dimethylformamide, to produce a coumarin-PEG$_n$-aminopropargyl-ddNTP.

In an embodiment, the aminopropargyl-ddNTP in step c) is a 5-aminopropargyl-ddNTP if the ddNTP comprises a cytosine, uracil, or thymidine base, and wherein the aminopropargyl-ddNTP in step c) is a 7-aminopropargyl-ddNTP if the ddNTP comprises an adenine or guanine base.

In an embodiment of the invention, n is 16, 20, 24, or 36.

In a further embodiment, the labeled terminating NPP analogue is a nucleotide analogue selected from the groups consisting of

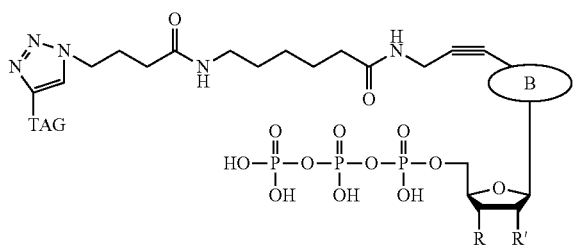

wherein BASE is selected from the group adenine, cytosine, thymine, uracil, guanine, 7-deaza-adenine, and 7-deaza-guanine or analog thereof;

R and R' can be independently H, OH, O-alkyl, F, Cl, Br, $N_3$, $NH_2$, O—$NH_2$, O-allyl, O—$CH_2N_3$, 2', 3'-isopropylidine or groups which only allow a single nucleotide to be incorporated by DNA polymerase;

TAG can be any polymeric molecule that can be detected by nanopore and may be selected from the group oligonucleotides, peptides, carbohydrates, and PEGs of different length.

The invention also provides for a process for producing a polymer tagged ddNTP analogue, comprising:
a) contacting a 5(7)-propargylamino-ddNTP with amino-protected caproic acid NHS ester;
b) reacting the product of step a) with ammonium hydroxide to produce 5(7)-propargylamidoaminocaproyl-ddNTPs;
c) reacting the product of step b) with azidobutyric acid NHS ester; and
d) reacting the product of step c) with 5'-alkynyl-oligonucleotide tag to produce oligonucleotide tagged ddNTPs The invention also provides for a dideoxynucleotide tetraphosphate (ddN4P) analogue, comprising a coumarin-polyethylene glycol (PEG)-aminopropargyl label attached to the terminal phosphate thereof.

In an embodiment of the invention, the ddN4P analogue has the structure comprises a different base and a unique polymeric tag, and each tag has a different composition and number of monomers.

In an embodiment of the invention, wherein the four ddN4P analogues are a ddA4P analogue, a ddG4P analogue, a ddC4P analogue, and either a ddT4P analogue or a ddU4P analogue.

The invention also provides for a process for producing a ddN4P analogue of the invention, comprising:
a) contacting a ddN4P with diaminoheptane in carbodiimide (EDAC) and imidazole buffer under conditions permitting the diaminoheptane to attach to the terminal phosphate;
b) contacting a 6-methoxycoumarin N-hydroxysuccinimidyl ester (NHS) with an amino-$PEG_n$-acid moiety in dimethylformamide, wherein n is the number of ethylene glycol monomers in the PEG, under conditions permitting the production of a coumarin-$PEG_n$-acid compound;
c) reacting the product of step b) with N,N disuccinimidyl carbonate in dimethylformamide, under conditions permitting the production of a coumarin-$PEG_n$-NHS compound; and
d) reacting the products of steps a) and c) to produce a coumarin-$PEG_n$-ddN4P analogue.

In an embodiment, the process further comprises, prior to step a), reacting a ddNTP with tributylammonium phosphate in order to obtain the ddN4P.

The invention also provides for a process for producing the ddG4P analogue of the invention, comprising:
a) contacting a ddG4P with diaminoheptane in carbodiimide (EDAC) and imidazole buffer under conditions permitting the diaminoheptane to attach to the terminal phosphate;
b) contacting a 6-methoxycoumarin N-hydroxysuccinimidyl ester (NHS) with an amino-$PEG_n$-acid moiety in dimethylformamide, wherein n is the number of ethylene glycol monomers in the PEG, under conditions permitting the production of a coumarin-$PEG_n$-acid compound;
c) reacting the product of step b) with N,N-disuccinimidyl carbonate in dimethylformamide, under conditions permitting the production of a coumarin-$PEG_n$-NHS compound; and
d) reacting the products of steps a) and c) to produce a coumarin-$PEG_n$-ddG4P analogue.

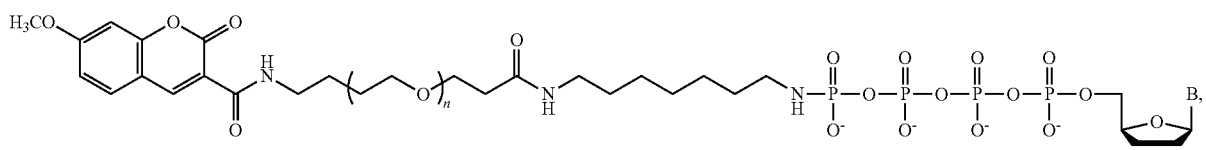

wherein n is 16, 20, 24, or 36, and wherein B is a base selected from the group consisting of adenine, cytosine, thymine, guanine, and uracil.

In an embodiment, the base is guanine.

The invention also provides for a composition comprising four ddN4P analogues of the invention, wherein each ddN4P In an embodiment, the process further comprises, prior to step a), reacting a ddGTP with tributylammonium phosphate in order to obtain the ddG4P.

The invention also provides for a dideoxynucleotide triphosphate (ddNTP) analogue, comprising a coumarin-polyethylene glycol (PEG)-aminopropargyl label attached to the base thereof.

In an embodiment, the ddNTP analogue has the structure:

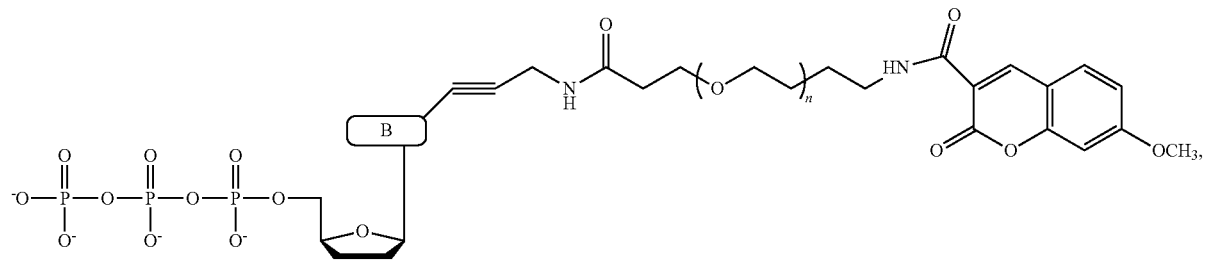

wherein B is a base selected from the group adenine, cytosine, thymine, guanine, and uracil or derivatives thereof; and n is 16, 20, 24, or 36.

The invention also provides for a composition comprising four ddNTP analogues of the invention, wherein each ddNTP comprises a different base and a unique polymeric tag, and each tag has a different composition and number of monomers.

In a further embodiment, the four ddNTP analogues are a ddATP analogue, a ddGTP analogue, a ddCTP analogue, and either a ddTTP analogue or a ddUTP analogue.

The invention also provides for a process for producing a ddNTP analogue of the invention, comprising:
  a) contacting a 6-methoxycoumarin N-hydroxysuccinimidyl ester (NHS) with an amino-PEG$_n$-acid moiety in dimethylformamide, wherein n is the number of ethylene glycol monomers in the PEG, under conditions permitting the production of a coumarin-PEG$_n$-acid compound;
  b) reacting the product of step a) with N,N disuccinimidyl carbonate in dimethylformamide, under conditions permitting the production of a coumarin-PEG$_n$-NHS compound; and
  c) reacting the product of step b) with an aminopropargyl-ddNTP, wherein the aminopropargyl moiety is base-attached, in dimethylformamide, to produce a coumarin-PEG$_n$-aminopropargyl-ddNTP.

In an embodiment, the aminopropargyl-ddNTP in step c) is a 5-aminopropargyl-ddNTP if the ddNTP comprises a cytosine, uracil, or thymidine base, and wherein the aminopropargyl-ddNTP in step c) is a 7-aminopropargyl-ddNTP if the ddNTP comprises an adenine or guanine base.

In an embodiment of the invention, n is 16, 20, 24, or 36.

In a further embodiment, the labeled terminating NPP analogue is a nucleotide analogue selected from the groups consisting of:

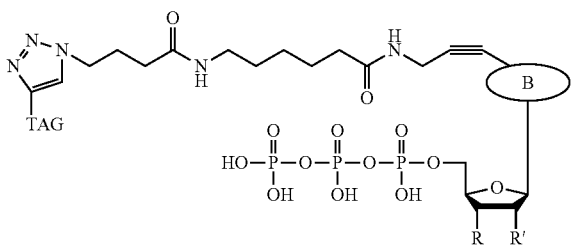

wherein BASE is selected from the group adenine, cytosine, thymine, uracil, guanine, 7-deaza-adenine, and 7-deaza-guanine or analog thereof;

R and R' can be independently H, OH, O-alkyl, F, Cl, Br, N$_3$, NH$_2$, O—NH$_2$, O-allyl, O—CH$_2$N$_3$, 2', 3'-isopropylidine or groups which only allow a single nucleotide to be incorporated by DNA polymerase;

TAG can be any polymeric molecule that can be detected by nanopore and may be selected from the group oligonucleotides, peptides, carbohydrates, and PEGs of different length.

The invention also provides for a process for producing a polymer tagged ddNTP analogue, comprising:
  a) contacting a 5(7)-propargylamino-ddNTP with amino-protected caproic acid NHS ester;
  b) reacting the product of step a) with ammonium hydroxide to produce 5(7)-propargylamidoaminocaproyl-ddNTPs;
  c) reacting the product of step b) with azidobutyric acid NHS ester; and
  d) reacting the product of step c) with 5'-alkynyl-oligonucleotide tag to produce oligonucleotide cagged ddNTPs.

The invention also provides for a process for producing a dNTP analogue with the tag attached on the base, comprising:
  a) contacting a 5(7)-propargylamino-dNTP with amino-protected caproic acid NHS ester;
  b) reacting the product of step a) with ammonium hydroxide to produce 5(7)-propargylamidoaminocaproyl-dNTPs;
  c) reacting the product of step b) with azidobutyric acid NHS ester; and
  d) reacting the product of step c) with 5'-alkynyl-oligonucleotide tag to produce oligonucleotide tagged dNTPs The invention also provides for a process of using dNTP analogues with distinct tags attached to the terminal phosphate (Fuller et al. 2015) for SNP detection by the heretofore described approach.

The invention also provides for an alpha hemolysin protein, having a primer conjugated thereto.

In an embodiment, the alpha hemolysin comprises a C46 mutation, and the primer is conjugated to the cysteine residue at position 46.

The invention also provides for a process for producing the primer-conjugated α-hemolysin of the invention, comprising:
  a) contacting a sulfosuccinimidyl-4-(N-maleimidomethyl) cyclohexane-1-carboxylate (sSMCC) hetero bifunctional crosslinker, comprising an amido-reactive N-hydroxysuccinimide (NHS) ester and a thiol-reactive maleimide group at opposite ends, with a primer comprising a terminal amino group, under conditions permitting the terminal amino group to react with the amido-reactive NHS ester;

b) removing residual unreacted sSMCCs from the solution; and c) contacting the product resulting from step a) with an α-hemolysin, wherein the α-hemolysin comprises a cysteine mutation at position 46, under conditions permitting the thiol-reactive maleimide group to react with the cysteine residue at position 46;

thereby conjugating the primer to the α-hemolysin.

In an embodiment, the removal of unreacted free sSMCCs in step b) is performed via purification by gel filtration.

The invention also provides for a conductance measurement system comprising:

a) an electrically resistive barrier separating at least a first and a second electrolyte solution;

said electrically resistive barrier comprises at least one pore with a diameter on nanometer scale;

said at least one pore being configured to allow an ionic current to be driven across said first and second electrolyte solutions by an applied potential;

b) at least one at least one labeled terminating nucleotide polyphosphate (NPP) analogue, wherein the label is attached to either the base or the terminal phosphate of the NPP analogue, in at least one of said first and second electrolyte solutions; and c) a means of measuring the ionic current and a means of recording its time course as a time series, including time periods when at least one pore is unobstructed by the label and also time periods when a label causes pulses of reduced-conductance.

In a further embodiment, the labeled terminating NPP analogue is a ddNPP analogue selected from the group consisting of

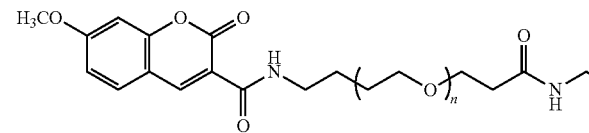

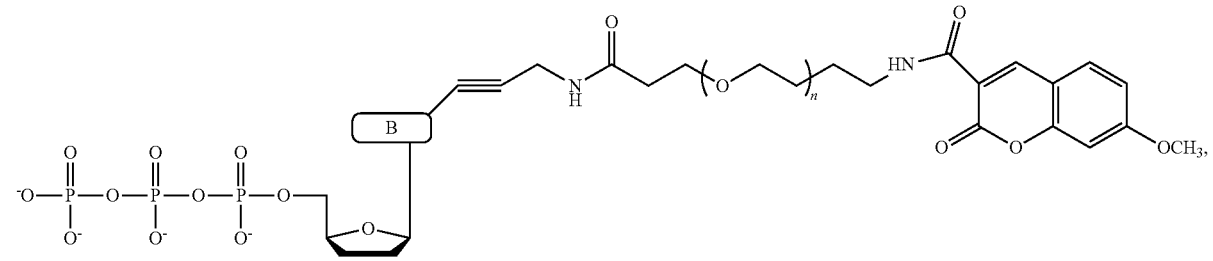

and

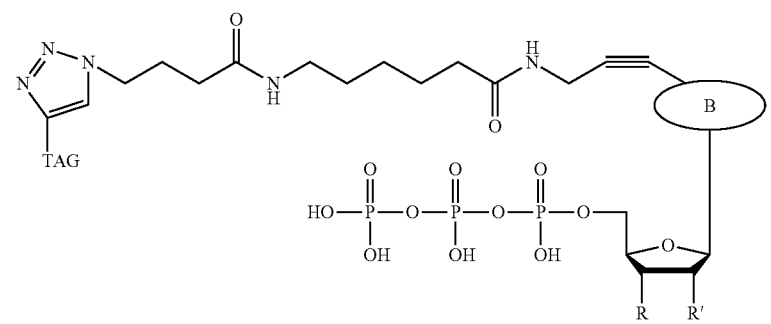

wherein B (BASE) is a base selected from the group adenine, cytosine, thymine, guanine, and uracil or derivatives thereof; and n is 16, 20, 24, or 36.

TAG can be any polymeric molecule that can be detected by nanopore and may be selected from the group oligonucleotides, peptides, carbohydrates, and PEGs of different length.

In an embodiment, the system comprises four ddNPP analogues having the structure

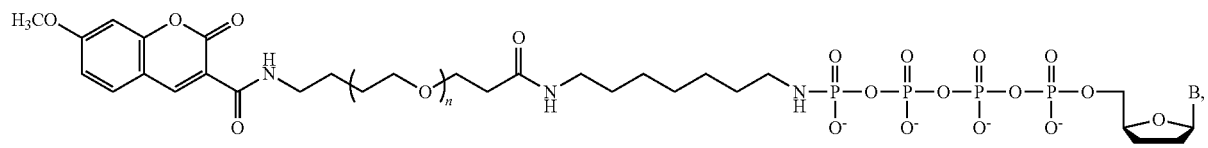

wherein each ddNTP comprises a different base, and each has a different value of n.

In an embodiment, the system comprises four ddNPP analogues having the structure

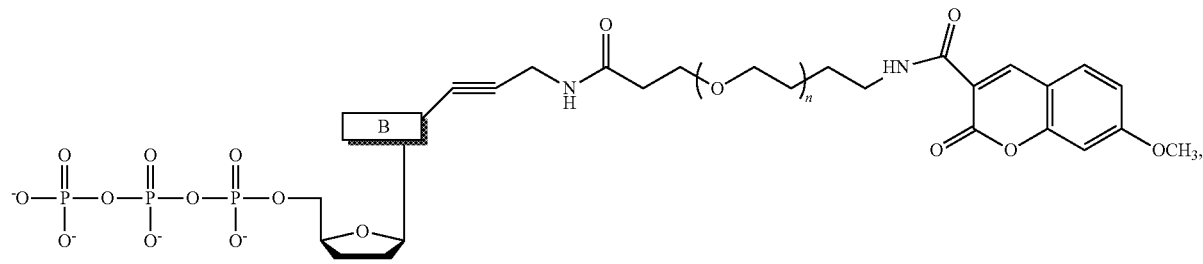

wherein each ddNTP comprises a different base, and each has a different value of n.

In an embodiment, the system comprises four ddNTP analogues which are a ddATP analogue, a ddGTP analogue, a ddCTP analogue, and either a ddTTP analogue or a ddUTP analogue.

As used herein, "alkyl" includes both branched and straight-chain saturated aliphatic hydrocarbon groups having the specified number of carbon atoms and may be unsubstituted or substituted. Thus, $C_1$-$C_n$ as in "$C_1$-$C_n$ alkyl" is defined to include groups having 1, 2, ..., n- or n carbons in a linear or branched arrangement. For example, a "$C_1$-$C_5$ alkyl" is defined to include groups having 1, 2, 3, 4, or 5 carbons in a linear or branched arrangement, and specifically includes methyl, ethyl, n-propyl, isopropyl, n-butyl, t-butyl, and pentyl.

As used herein, "alkenyl" refers to a non-aromatic hydrocarbon group, straight or branched, containing at least 1 carbon to carbon double bond, and up to the maximum possible number of non-aromatic carbon-carbon double bonds may be present, and may be unsubstituted or substituted. For example, "$C_2$-$C_5$ alkenyl" means an alkenyl group having 2, 3, 4, or 5, carbon atoms, and up to 1, 2, 3, or 4, carbon-carbon double bonds respectively. Alkenyl groups include ethenyl, propenyl, and butenyl.

The term "alkynyl" refers to a hydrocarbon group, straight or branched, containing at least 1 carbon to carbon triple bond, and up to the maximum possible number of non-aromatic carbon-carbon triple bonds may be present, and may be unsubstituted or substituted. Thus, "$C_2$-$C_5$ alkynyl" means an alkynyl group having 2 or 3 carbon atoms and 1 carbon-carbon triple bond, or having 4 or 5 carbon atoms and up to 2 carbon-carbon triple bonds. Alkynyl groups include ethynyl, propynyl and butynyl.

The term "substituted" refers to a functional group as described above such as an alkyl, or a hydrocarbyl, in which at least one bond to a hydrogen atom contained therein is replaced by a bond to non-hydrogen or non-carbon atom, provided that normal valencies are maintained and that the substitution(s) result(s) in a stable compound. Substituted groups also include groups in which one or more bonds to a carbon(s) or hydrogen(s) atom are replaced by one or more bonds, including double or triple bonds, to a heteroatom. Non-limiting examples of substituents include the functional groups described above, and for example, N, so as to form —CN.

Exemplary Labels

A label (also referred to herein as a tag) may be any chemical group or molecule that is capable of being detected in a nanopore. In one embodiment, a label provides an electronic signature by blocking or impeding ionic current through a nanopore.

In some cases, a label comprises one or more of ethylene glycol, an amino acid, a carbohydrate, a peptide, a dye, a chemiluminescent compound, a mononucleotide, a dinucleotide, a trinucleotide, a tetranucleotide, a pentanucleotide, a hexanucleotide, an oligonucleotide (modified or unmodified), an aliphatic acid, an aromatic acid, an alcohol, a thiol group, a cyano group, a nitro group, an alkyl group, an alkenyl group, an alkynyl group, an azido group, or a combination thereof.

In some cases, the label is a polymer. Polyethylene glycol (PEG) is an example of a polymer and has the following structure:

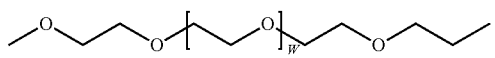

Any number of ethylene glycol units (W) may be used. In some cases, each label is a PEG label comprising a different number of ethylene glycol units.

Nanopore Detection of Labels

Previously, Kasianowicz et al. (1996) discovered that the α-hemolysin (αHL) protein nanopore, which has a 1.5 nm-diameter limiting aperture (Song et al. 1996, Bezrukov et al. 1996, Krasilnikov 2002, and Kasianowicz et al. 1995), could be used to electronically detect nucleic acids at the single molecule level. Thus, the αHL nanopore has been investigated widely for the development of a single molecule electronic DNA sequencing technology (Kasianowicz et al. 1996, Kasianowicz et al. 2002, Kasianowicz et al. 1998, and Clarke et al. 2009). The majority of these research efforts involve strand DNA sequencing by nanopore, which aim at sequencing DNA by threading it through the nanopore and detecting the electrical current blockade from the 4 nucleotides (A, C, G, T) (Cherf et al. 2012 and Manrao et al. 2012).

The native αHL nanopore has an intrinsic property for high-resolution discrimination of molecules and ions, which enables the discrimination between aqueous $H^-$ and $D^+$ ions (Kasianowicz et al. 1995). Robertson et al. (2007) have demonstrated that the αHL nanopore can easily separate more than 20 different PEG polymers at single monomer level. This study indicates that the mean residence time of the PEG polymer in the pore increases with its size (Reiner et al. 2010). Recently, Kumar et al. (2012) have reported the use of 4 PEGs of distinct size to label the terminal phosphate of nucleotides for single molecule electronic DNA sequencing by synthesis with nanopore detection. Based on these previous investigations, the single molecule electronic multiplex SNP assay described herein will be capable of detecting multiple genetic variations simultaneously using PEGs of different sizes to tag nucleotides.

This invention will be better understood by reference to the Experimental Details which follow, but those skilled in the art will readily appreciate that the specific experiments are only illustrative of the invention as described more fully in the claims which follow thereafter. Every embodiment and feature described in the application should be understood to be interchangeable and combinable with every embodiment contained within.

Experimental Details and Discussion

Review of SNP Analysis Via MALDI-TOF MS

The early SBE method for multiplex SNP analysis using MALDI-TOF MS detected both primers and their extension products, because both were loaded to the MS analyzer. This requires the unambiguous simultaneous detection of multiplex primers and their extension products. However, for longer biopolymers, such as DNA, MALDI-TOF MS analyzer has limitations in resolution and sensitivity. As a result, larger DNA molecules could not be resolved by MALDI-TOF MS. To address this issue, Kim et al. developed a multiplex SNP assay (SPC-SBE) using solid phase capturable (SPC) biotinylated dideoxynucleotide terminators (biotin-ddNTPs) in SBE by detection with MALDI-TOF MS (Kim et al. 2002 and Kim et al. 2003).

In the SPC-SBE method, a library of oligonucleotide primers corresponding to the multiple SNP sites are designed to have different molecular mass. These primers are then annealed to the SNP sites of the target gene and extended with a specific biotin-ddNTP by DNA polymerase, producing 3'-biotinylated DNA products. Treatment of the polymerase reaction mixtures by streptavidin-coated magnetic beads leads to the capture of the DNA products that carry a biotin moiety at the 3'-end. The excess primers, DNA polymerase and salts in the reaction are washed away. The pure DNA extension products are subsequently released from the magnetic beads by denaturing the biotin-streptavidin interaction with formamide at 95° C., and characterized with MALDI-TOF MS for SNP determination. In the SPC-SBE approach, the accuracy and scope of multiplexing in SNP analysis is significantly increased, because only the isolated primer extension products are loaded into the MALDI-TOF MS analyzer. Consequently, the resulting mass spectrum is free of the non-extended primer peaks and their associated dimers, which do not carry a biotin moiety and are removed during SPC. SPC also facilitates desalting of the captured DNA products and therefore enhances the accuracy and the overall quality of the MS data for SNP analysis.

In summary, in the SPC-SBE multiplex SNP assay with MALDI-TOF MS (Kim et al. 2002), multiplex PCR products are produced as templates from genomic DNA for carrying out SBE reactions using SNP specific primers with different mass. Only the DNA extension products extended by a specific biotin-ddNTP are captured while the other components of the reaction are removed. The captured DNA products are then released and loaded on to the MALDI-TOF MS analyzer to identify nucleotide variation. It has been shown that unextended primers occupy the effective mass range in the mass spectrum reducing the ability for multiplexing. The excess primers can form a dimer, producing false peaks in the mass spectrum (Roskey et al. 1996). All the above complications are completely removed by the SPC-SBE. Due to the large molecular weight difference of the four biotin-ddNTPs, polymerase extension products from these dideoxynucleotides are unambiguously detected with well resolved molecular weights. The molecular weight of the primer extension products in comparison to the masses of the corresponding primers reveal the identity of each nucleotide at the polymorphic site. The SPC-SBE method is particularly beneficial in determining heterozygous genotypes. In this case, two peaks, one corresponding to each allele, will be clearly discernible in the resulting mass spectrum.

MALDI-TOF MS, when used for characterizing SNPs, can simultaneously measure the masses of DNA molecules over a certain range. To make best use of this feature for the analysis of multiple SNPs in a single MS spectrum, if excess primers are not removed, masses of all primers and their extension products have to be sufficiently different to produce peaks that can be adequately resolved in the mass spectrum. For example, Ross et al. (1998) performed simultaneous detection of multiple SNPs by tuning the masses of all primers and their extension products so that they would lie in the range of 4.5 kDa and 7.6 kDa with no overlapping. In contrast, by eliminating the unextended primers that occupy the valuable mass range in the mass spectrum, the SPC-SBE approach significantly increases the scope of multiplexing in characterization of SNPs. Genetic variations (C282Y and H63D) in the human hereditary hemochromatosis gene were successfully and accurately characterized by SPC-SBE (Kim et al. 2002). Thirty polymorphic sites in exons 5, 7 and 8 of the tumor suppressor gene p53, which are most frequently mutated in human cancer (Hollstein et al.

1991 and Bardelli et al. 2003), from Wilms' tumors, head and neck squamous carcinomas as well as colorectal carcinomas, were also precisely determined with the SPC-SBE method (Kim et al. 2004). Using the SPC-SBE approach, Misra et al. performed concurrent analysis of 40 SNPs of CYP2C9 and 50 SNPs of CYP2A13 in the cytochrome P450 (CYP450) genes (Misra et al. 2007).

DNA purification exploiting the strong interaction of a small molecule, biotin, and a protein, streptavidin on solid surfaces such as magnetic beads is extensively used in biotechnology. However, the affinity between biotin and streptavidin is among the strongest known non-covalent bonds. The denaturing of the biotin-streptavidin interaction requires treatment with formamide at 95° C. and the reaction yield is often low. To further optimize the condition for SPC and release of the DNA extension products from streptavidin-coated magnetic beads, Qiu et al. (Anal. Biochem, 427:193-201, 2012) developed a set of chemically cleavable biotinylated dideoxynucleotides, ddNTPs-$N_3$-Biotin (ddATP-$N_3$-Biotin, ddGTP-$N_3$-Biotin, ddCTP-$N_3$-Biotin and ddUTP-$N_3$-Biotin), for application in DNA sequencing and SNP analysis by MALDI-TOF MS. These cleavable biotinylated dideoxynucleotides have been successfully used in SPC-SBE to characterize mitochondrial SNPs (Qiu et al., Anal. Biochem, 427:202-210, 2012).

Several alternative methods for multiplex SNP analysis that use mass spectrometry have been developed. For example, the commercially available MASSARRAY™ assay (Rodi et al. 2002) from Sequenom Inc. is widely used for characterizing genetic variations, including mitochondrial SNPs for population studies (Cerezo et al. 2009) and detection of heteroplasmy (Xiu-Cheng et al. 2008). The MASSARRAY™ assay is automated with high throughput. In one form of this approach, the primer is extended by DNA polymerase in the presence of three dideoxynucleotides and one deoxynucleotide that corresponds to one of the two alleles. At the end of the reaction, single nucleotide primer extension products and the primers extended with two or more nucleotides as well as the unextended primers are all loaded on to the MALDI-TOF MS analyzer and detected in the mass spectrum. Since no labeling of any reaction components is required, the MASSARPAY™ assay is simple to perform. However, it is limited in performing simultaneous high level multiplex analysis of SNPs, because all reaction products and all unextended primers are both loaded into the MS analyzer.

Review of SNP Analysis by Fluorescence Detection

The fluorescence polarization-template-directed dye-terminator incorporation (FP-TDI) SNP assay (Chen et al. 1999) uses single nucleotide polymerase extension with allele-specific fluorescence-labeled dideoxynucleotide terminators. The genotypes of the extension products are characterized by monitoring the unique change in fluorescence polarization. The FP-TDI approach offers a simple SNP detection method but with a limited scope of multiplexing.

The BEAMing (beads, emulsion, amplification, and magnetics) approach (Dressman et al. 2003) has been developed for detecting genetic variations with the aim of high-sensitivity and high-throughput. In this method, each individual DNA template is discretely amplified by a large number of oligonucleotide primers that are immobilized on a magnetic bead in a water-oil emulsion, the target SNPs are distinguished by unique fluorescent dye-labeled probes and characterized using flow cytometry. The BEAMing approach not only allows the identification of allelic variations, but also offers the ability to quantify these variations. In addition, the DNA sample can be recovered from the flow cytometer for further analysis. The disadvantage of the BEAMing method is that multiple steps of manipulation are required, which can lead to difficulties in accurate characterization of allele frequency.

Tong et al. have developed a multiplex fluorescent SNP assay using SBE and combinatorial fluorescence energy transfer (CFET) tags (Tong et al. 2002). A larger number of CFET tags with unique fluorescence signatures have been constructed using a small number of fluorophores with distinct emissions by exploiting fluorescence energy transfer and the combinatorial concept. The CFET tags can all be excited at a single wavelength of 488 nm and detected and differentiated by a simple optical system. The principle of the approach is outlined as follows. A library of CFET-labeled oligonucleotide primers are designed and synthesized so that the nucleotide at the 3'-end is complementary to a particular SNP in the template. In a single tube reaction, the CFET-labeled oligonucleotide primers and biotin-ddNTPs are used to perform SBE on the DNA templates containing the SNPs. CFET-labeled primer that perfectly matches with the DNA template is extended with a biotin-ddNTP by DNA polymerase. The 3'-biotinylated DNA products are isolated by capture with streptavidin-coated magnetic beads, while the unextended primers and other components in the reaction are not captured and eliminated by washing. A multicolor laser-induced fluorescence electrophoresis instrument is used to analyze the biotinylated fluorescent DNA products. The SNPs are determined by the distinct fluorescence signature and electrophoretic mobility of each DNA extension product in the electropherogram. Using oligonucleotide ligation, Tong et al. (2001) have used CFET tags to detect multiplex nucleotide variations simultaneously from the retinoblastoma tumor suppressor gene. None of the mass spectroscopy or fluorescence based approaches reviewed above offer detection of SNPs with single molecule sensitivity.

Experiment 1

Design and Synthesis of PEG-Labeled ddNTP Analogues for DNA Polymerase Extension In an embodiment of single molecule, single-base extension electronic SNP genotyping scheme described herein, current blockade signals in the nanopore are generated by the capture of PEG molecules that are attached to the nucleotides. Hence, the design and synthesis of PEG-labeled ddNTPs and test these molecules as substrates for DNA polymerases are required. It is necessary to find a unique position in the ddNTPs to attach the tags without interrupting the active sites of DNA polymerases and the native DNA structure during the nucleotide incorporation. To achieve this, two possible positions in ddNTPs are tested for the tag attachment: either the terminal phosphate or the specific position on the base in each nucleotide.

First, considering that pyrophosphate is released from the enzyme complex during the polymerase reaction, we reasoned that the terminal phosphate of each of the four nucleotides might be available for the attachment of longer polymer tags. Indeed, Kumar et al. (2012) have attached PEG molecules of different lengths to the terminal phosphate position of deoxyguanosine and demonstrated that these modified nucleotides are incorporated into primers with 100% efficiency for DNA sequencing. In detail, they added an extra phosphate to the deoxyguanosine triphosphate (dGTP) to serve as a linker between the γ-phosphate of dGTP and the tag, preventing the tag from interfering with the active site of the DNA polymerase during the incorporation. Then, four distinct PEG tags were attached, generating PEG tagged deoxyguanosine tetraphosphates (PEG-dG4P). They showed that these PEG-dG4P nucleotides are efficient substrates for DNA polymerase extension (Kumar et al. 2012). This result indicates that DNA polymerase can tolerate sizable modification at the terminal phosphate position of deoxynucleotide triphosphates (dNTPs), including the additional phosphate and the PEG tag, and utilize such nucleotide analogues as competent substrates for primer extension by polymerase. An earlier study had shown that DNA polymerases recognize tetra- or longer polyphosphates with improved efficiency (up to 50-fold) than the corresponding tri-phosphates (Kumar et al. 2005).

Figure 4:
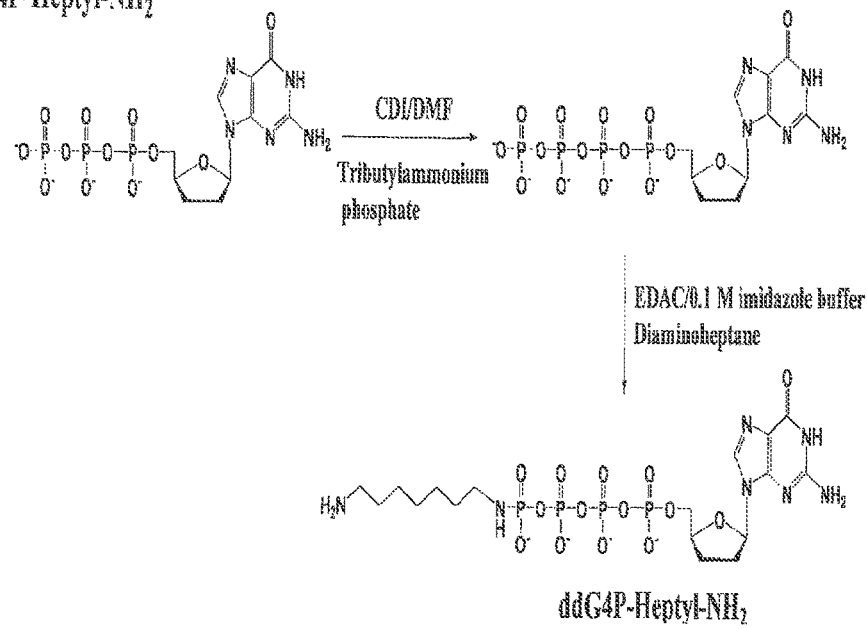
FIG. 4. Design and synthesis of the four coumarin-$PEG_n$-dideoxyguanosine-5'-tetraphosphates. The specific synthesis shown is for a ddG4P, but the same process can be used, mutatis mutandis, to produce other ddN4Ps.
Figure 4:
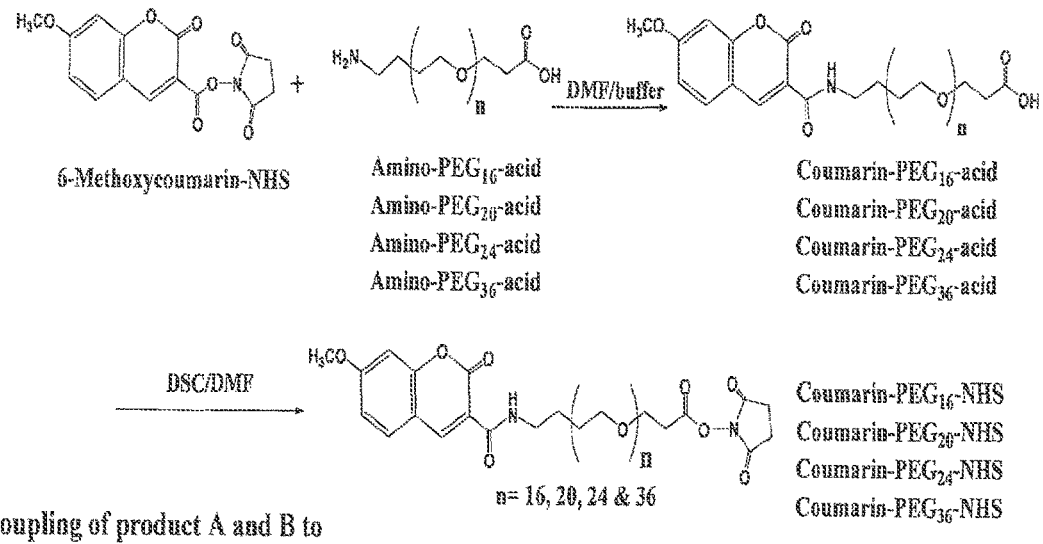
Figure 4:
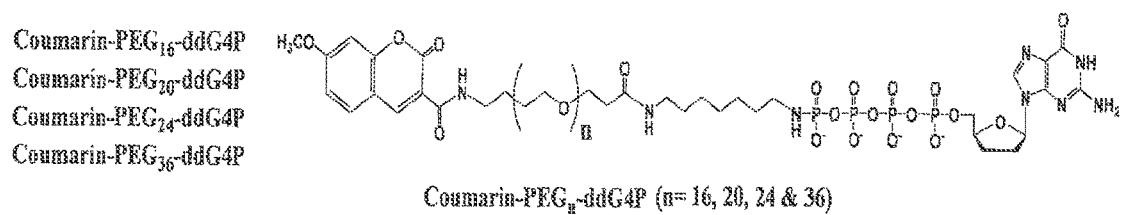

Thus, taking advantage of the above strategy, as an example, the present approach includes different length PEG molecules being attached to the terminal phosphate position in each ddNTP. The synthesis process is as follows. First, dideoxynucleoside triphosphates (ddNTPs) are converted to dideoxynucleoside tetraphosphates (ddN4Ps) by treatment with tributylammonium phosphate. Then, a diaminoheptane linker is added to the terminal phosphate of the tetraphosphate to produce ddN4P-heptyl-$NH_2$ (Product A) for attaching different length PEG tags. In a separate set of reactions, 6-methoxy-coumarin N-hydroxysuccinimidyl ester is reacted with one of four amino-$PEG_n$-COOH molecules, with n corresponding to 16, 20, 24, or 36 ethylene glycol units, to yield coumarin-$PEG_n$-COOH molecules, which are subsequently converted to the corresponding NHS-esters (Product B). The coumarin moiety is employed to track the purification of intermediates and the final nucleotide analogues. Finally, coupling of ddN4P-heptyl-$NH_2$ (Product A) with the coumarin-$PEG_n$-NHS esters (Product B) produces the final tagged nucleotide analogues. The PEG molecules with 16, 20, 24, or 36 ethylene glycol units are attached to A, C, G or T, respectively. An example of the synthesis scheme for the proposed coumarin-$PEG_n$-ddG4P molecule is provided in FIG. 4. Following the same scheme, a complete set of ddN4Ps (A, C, G, T), each of which is tagged with a unique PEG polymer, is synthesized.

Figure 5:
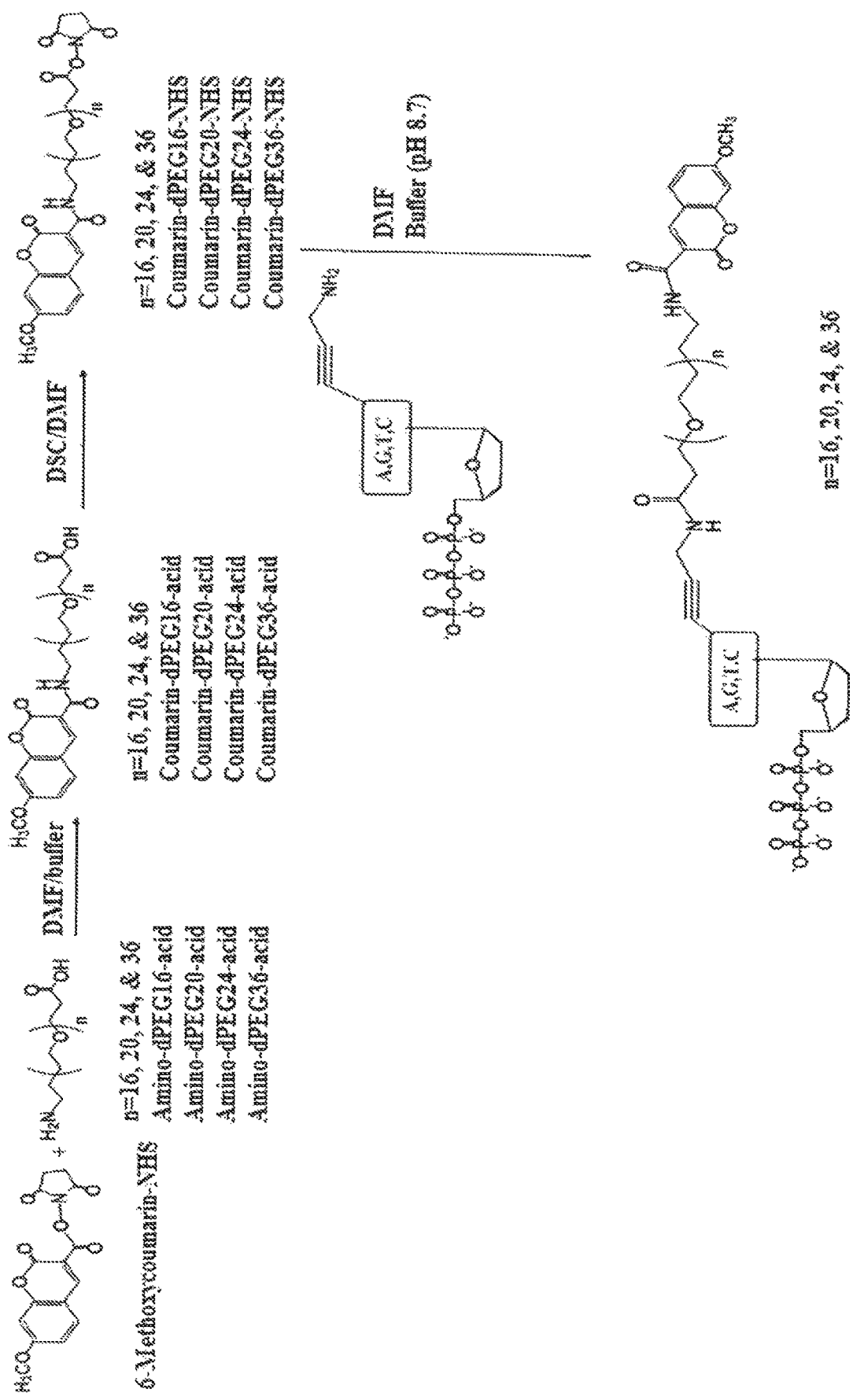
FIG. 5. Design and synthesis of the coumarin-$PEG_n$-aminopropargyl-ddNTPs.

Second, it has also been demonstrated that certain modified DNA polymerases can tolerate nucleotides with extensive modifications containing bulky groups at the 5-position of pyrimidines (C and U) and the 7-position of purines (A and G) (Rosenblum et al. 1997). Indeed, several nucleotides labeled with fluorescent dyes at the 5-position of pyrimidines or 7-position of purines have been created and employed for various genomic applications including DNA labeling and sequencing (Ju et al. 2006). Based on these previous studies, different length PEG tags are attached to the 5-position of C/U and the 7-position of A/G as an alternative design. In order to synthesize these molecules, 6-methoxycoumarin-NHS ester is reacted with one of the four amino-$PEG_n$-COOH molecules with 16, 20, 24, or 36 ethylene glycol units to yield coumarin-$PEG_r$-COOH molecules, which is subsequently converted to the corresponding NHS-esters. Then, the resulting coumarin-$PEG_n$-NHS-ester is coupled with 5-aminopropargyl-ddNTPs for C/U and 7-aminopropargyl-ddNTPs for A/G. The general synthesis scheme for the coumarin-$PEG_n$-aminopropargyl-ddNTPs is provided in FIG. 5. Additionally, different types of tags such as polymers of oligosaccharides, nucleotides, or oligopeptides can be synthesized and tested for improved nanopore signal resolution.

After synthesizing these molecules, their capability as substrates for DNA polymerase extension reactions are examined using a self-primed loop template DNA. If each compound is recognized and incorporated by DNA polymerase into the primer, the molecular weight of the primer will be increased by the size of the expected nucleoside monophosphate in the case of 5' phosphate tagging, or tagged nucleoside monophosphate in base-tagged molecules, and this can be detected by MALDI-TOF mass spectroscopy.

Synthesis of Oligonucleotide-Tagged Nucleoside Polyphosphates

Figure 6:
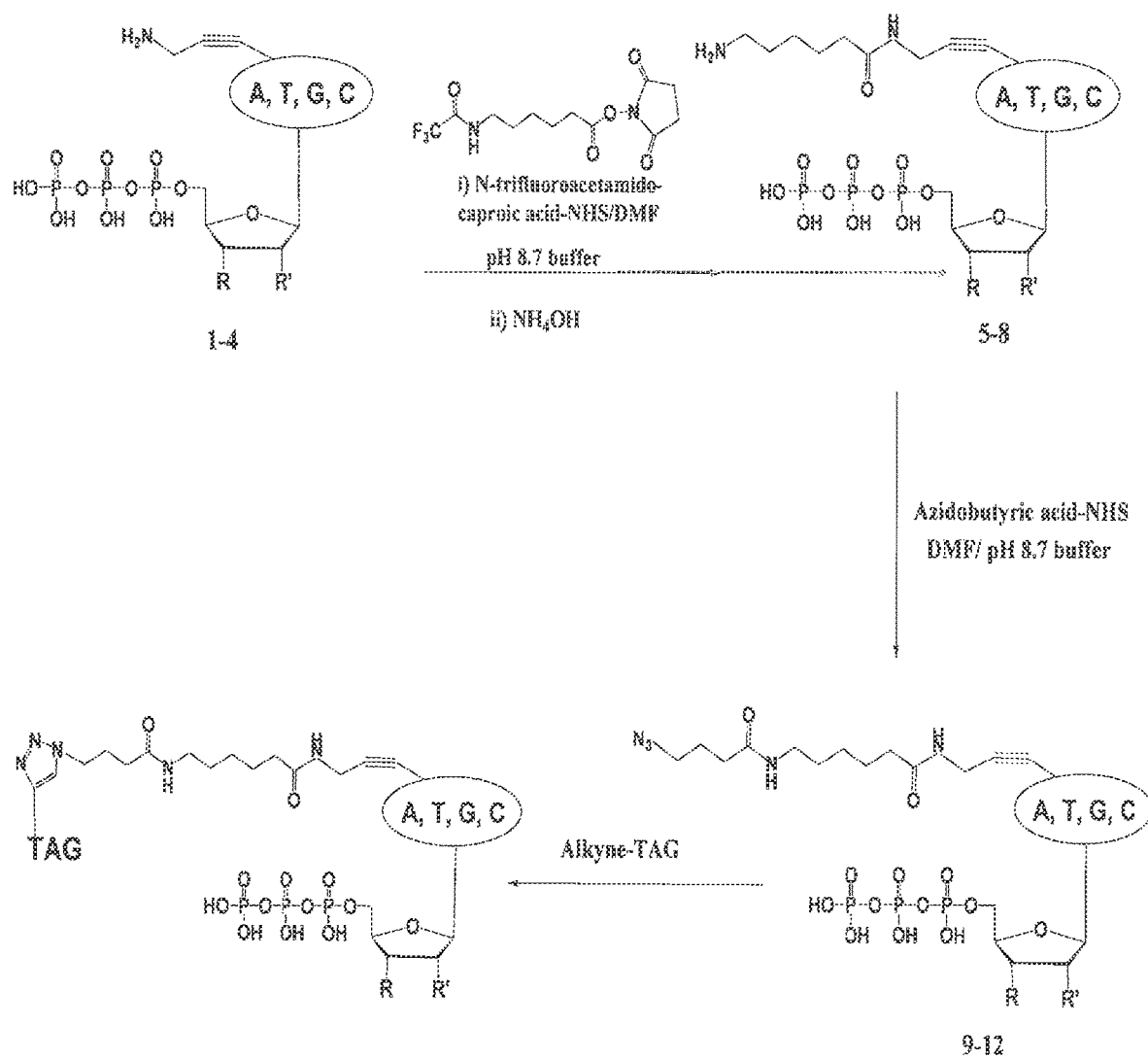
FIG. 6. Design and synthesis of oligonucleotide-tagged aminopropargyl-ddNTPs.

The general overall synthetic scheme is presented in FIG. 6. Synthesis of the oligonucleotide-tagged nucleotides involves the coupling 5(7)-alkynylamino-2'-3'-dideoxynucleoside-5'-triphosphate-azides (ddNTP-N3) with 5'-hexynyl oligonucleotides.

Synthesis of 5 or 7-Propargylamidoaminocaproyl-ddNTPs (5-8).

The 5(7)-propargylamino-dideoxynucleotides (1-4) were prepared following the procedure described by Hobbs and Cocuzza (1991) and the longer linker arm dideoxynucleotides (5-8) were prepared according to Duthie et al. (2002) and purified by reverse phase HPLC.

Addition of Azido Group to 5 or 7-Propargylamidoaminocaproyl-ddNTPs (9-12)

The extended ddNTP-NH2 nucleotides (5-8, 5 μmol) were each dissolved in 0.1 M bicarbonate-carbonate buffer (200 μl, pH 8.7) and azidobutyric acid-NHS (15 μmol) in 100 μl DMF was added. The reaction mixture was stirred overnight at room temperature and was purified by HPLC using 0.1 M TEAC buffer (pH 7.5) and an acetonitrile gradient to yield products 9-12. MALDI TOF MS data: ddATP-N3: 750 (calculated 751); ddUTP-N3: 726 (calculated 729); ddGTP-N3: 765 (calculated 767); ddCTP-N3: 725 (calculated 728).

Figure 7:
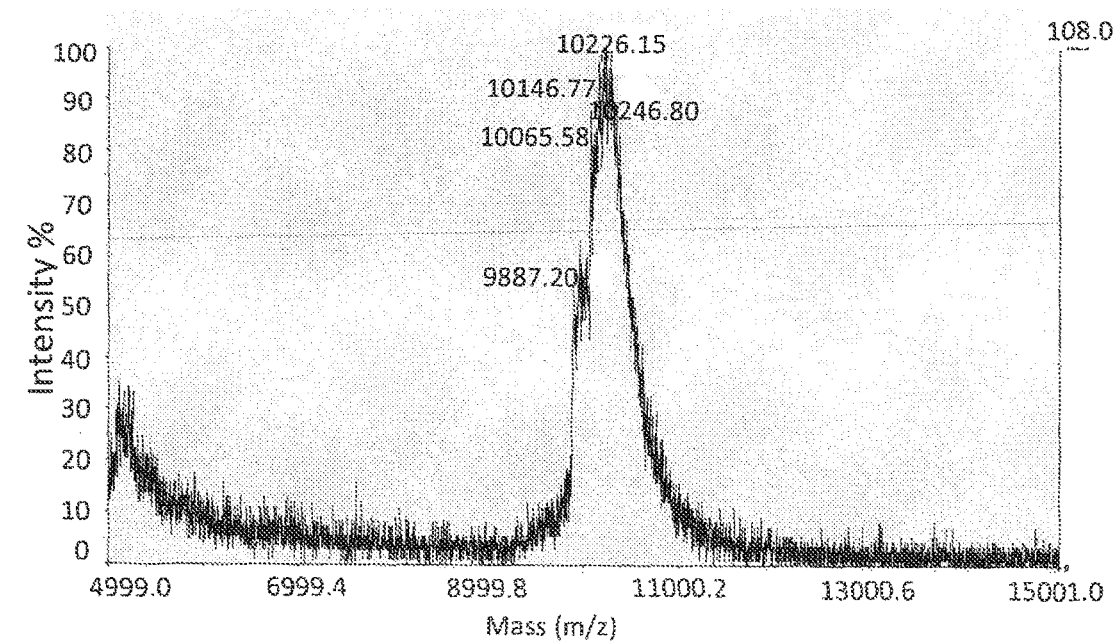
FIG. 7. MALDI-TOF MS measurements and structures of oligonucleotide-tagged aminopropargyl-ddTTP (ddTTP-Cy3-$T_4$-$dSp_3$-$T_{23}$-C3) and -ddCTP (ddCTP-Cy3-$T_2$-$dSp_8$-$T_{20}$-C3).
Figure 7:
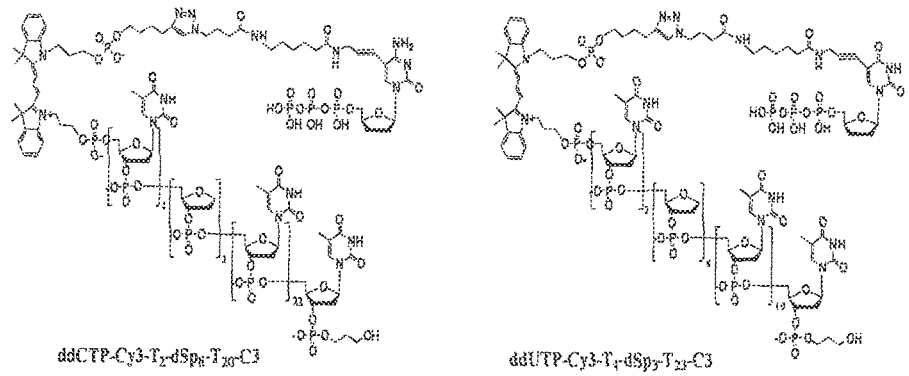
Figure 7:
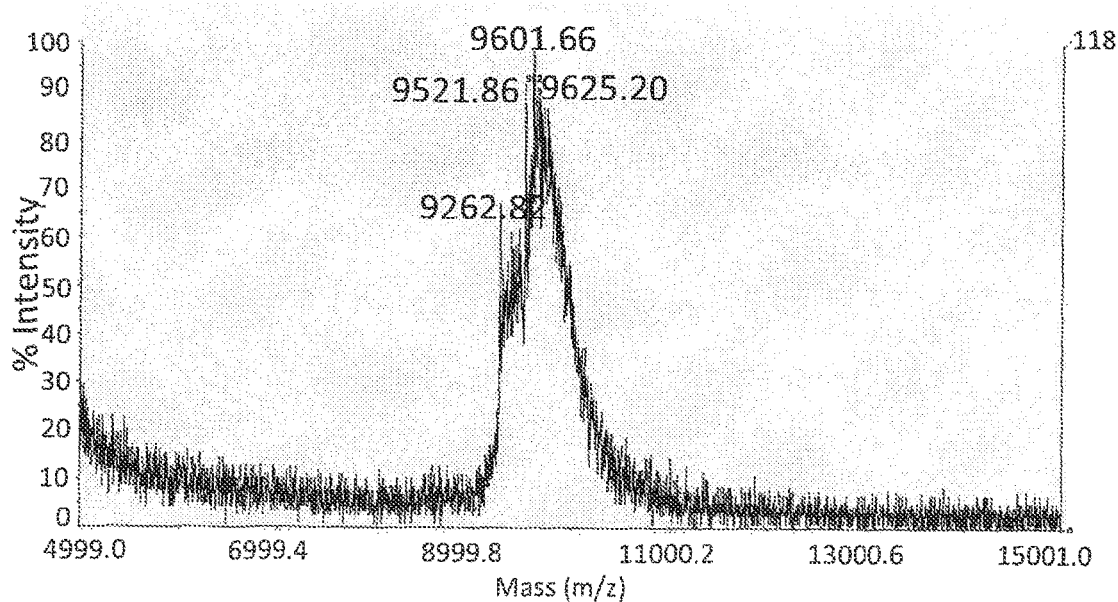

Click Reaction Between ddNTP-N3 Nucleotides (9-12) and 5'-Hexynyl Oligonucleotide Tags to Produce Polymer-Tagged ddNTP Nucleotides To each 5'-hexynyl-oligonucleotide tag (custom synthesized by TriLink, 500 nmol in 200 μl $H_2O$) was added a solution of the corresponding $ddNTP-N_3$ nucleotide (750 nmol) followed by the addition of copper bromide (50 μl, 0.1 M solution in 3:1 DMSO/t-BuOH) and tris[(1-benzyl-1H-1,2,3-triazol-4-yl)methyl]amine (TBTA) (100 μl, 0.1 M solution in 3:1 DMSO/t-BuOH). The reaction mixture was stirred at 40° C. for 16 hr followed by HPLC purification using 0.1 M TEAC buffer (pH 7.5) and an acetonitrile gradient. The tagged nucleotides were characterized by MALDI-TOF mass spectroscopy and single base polymerase extension reaction. MALDI-TOF mass data for two of the tagged nucleotides are shown in FIG. 7: ddCTP-Cy3-$dT_2$-$dSp_8$-$dT_{20}$-C3, 9601 (calculated 9605); ddTTP-Cy3-$dT_4$-$dSp_3$-$dT_{20}$-C3, 10226 (calculated 10225).

Figure 8:
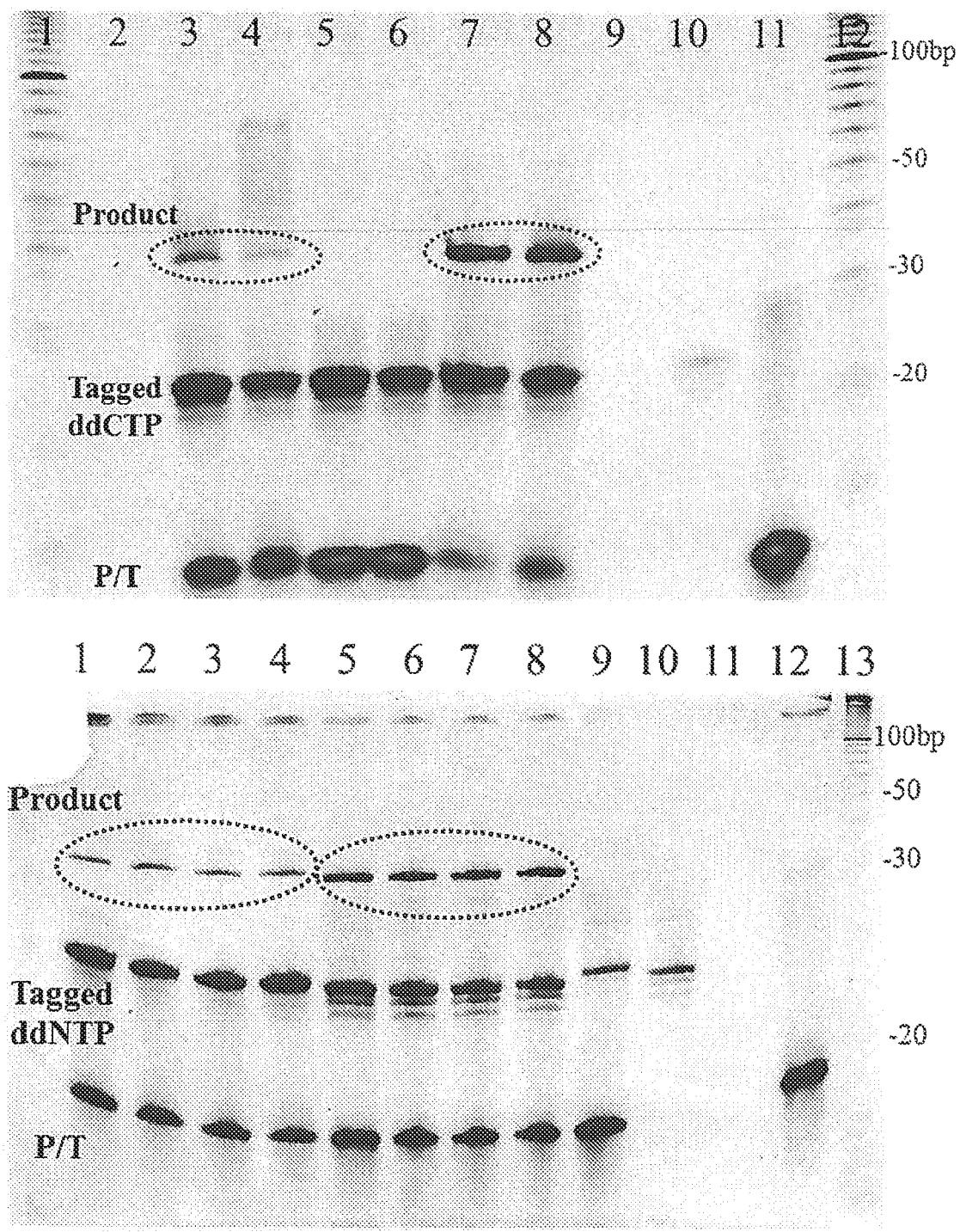
FIG. 8. Single-base polymerase extension reactions with oligonucleotide-tagged aminopropargyl-ddTTP and -ddCTP characterized by gel electrophoresis. Extension reactions were conducted in the presence of tagged ddCTP (top gel) and different enzymes including Klenow, Sequenase and Thermo Sequenase. Reactions are performed with 10 pmol of self-primed looped template (5'-GATAGCGCCGCGC-CTTGGCGCGGCGC-3') (SEQ ID No: 1), 200 pmol of tagged ddNTPs and 5 units of each enzyme incubated for 1 hr at 37° C. In the bottom gel, lanes 1-4 are extension reactions with tagged ddTTP and lanes 5-8 are reactions with tagged ddCTP using Thermo Sequenase. Lane 9 is a negative control extension reaction without the enzyme. Lanes 10 and 12 are tagged ddCTPs and primer-template controls respectively.

Single Base Extension Reactions with Oligonucleotide-Tagged ddCTP and Oligonucleotide-Tagged ddTTP Extension reactions were carried out using a template-loop primer in which the next complementary base on the template was either A or G, (allowing extension by a single complementary nucleotide. Reactions were performed with 10 μmol of self-primed looped template, 200 pmole of tagged ddNTPs and 5 units of each enzyme (Klenow, Sequenase and Thermo Sequenase) incubated for 1 hr at 37° C. DNA extension products were characterized by gel electrophoresis as shown in FIG. 8.

Method of Detection of SNPs Using Streptavidin-Biotin Capture

Figure 9:
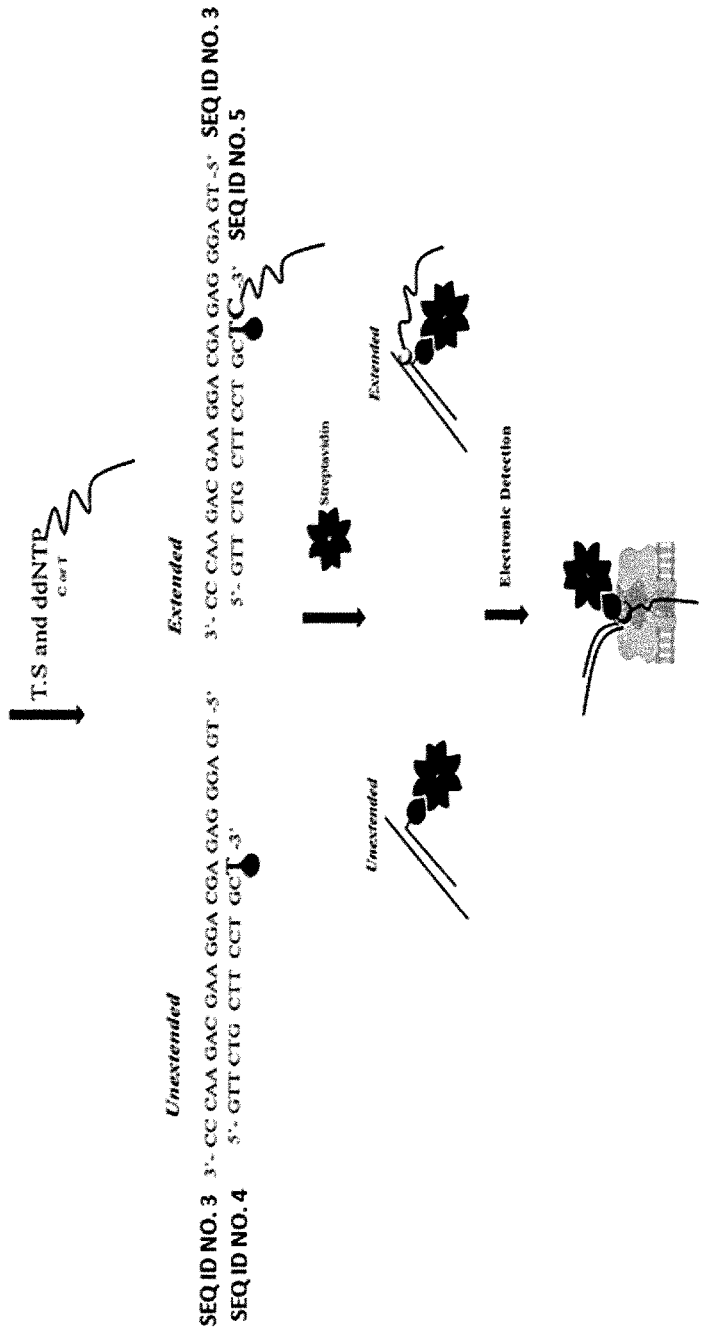
FIG. 9. Scheme for characterizing current signatures of different tags by extending biotinylated primers with tagged ddNTPs. Primers having a single biotin molecule attached to the base of the 3'-nucleotide and complementary template DNA are incubated with Thermo Sequenase, $Mg^{2+}$ and tagged ddNTPs. The DNA polymerase extends the primers with a single tagged ddNTP that is complementary to the next base in the template DNA. After the incubation, streptavidin molecules that have strong affinity for biotin are added to the extension reaction and both the unextended and extended primers are captured by the streptavidin. The reaction mixture is then applied to the nanopore electronic detection system. Although streptavidin itself cannot fit through the pore due to its much larger size, it holds the primer extension product in a position whereby the tag can enter the pore, generating a unique current signature specific for the tag on each nucleotide. In this way, the current signatures of different tags can be confirmed.

A scheme for characterizing current signatures of different tags by extending biotinylated primers with tagged ddNTPs is presented in FIG. 9. Primers having a single biotin molecule attached to the base of the 3'-nucleotide and complementary template DNA are incubated with Thermo Sequenase, $Mg^{2+}$ and tagged ddNTPs. The DNA polymerase extends the primers with a single tagged ddNTP that is complementary to the next base in the template DNA. After the incubation, streptavidin molecules that have strong affinity for biotin are added to the extension reaction and both the unextended and extended primers are captured by the streptavidin. The reaction mixture is then applied to the nanopore electronic detection system. Although streptavidin itself cannot fit through the pore due to its much larger size, it holds the primer extension product in a position whereby the tag can enter the pore, generating a unique current signature specific for the tag on each nucleotide. In this way, the current signatures of different tags can be confirmed.

Nanopore Current Blockade Levels of Tagged Nucleotides

Figure 10:
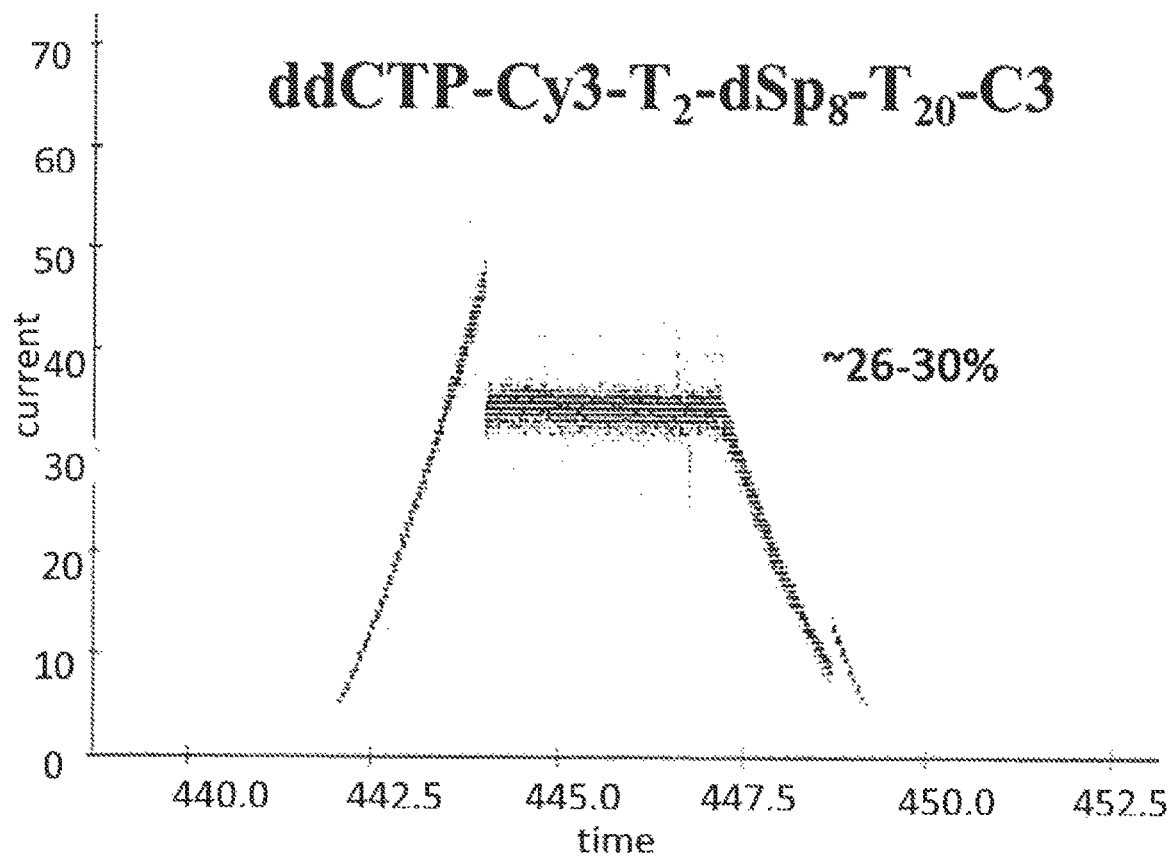
FIG. 10. Nanopore current blockade levels generated by the tags on the primer extension products by incorporating tagged ddCTP (ddCTP-Cy3-$T_2$-$dSp_8$-$T_{20}$-C3) and tagged ddTTP (ddTTP-Cy3-$T_4$-$dSp_3$-$T_{23}$-C3). The tag on the primer extension product incorporating a tagged ddCTP displayed a current blockade of about 26-30% of the open pore current level and the tag on the primer extension product incorporating a tagged ddTTP gave a 46-50% blockade.
Figure 10:
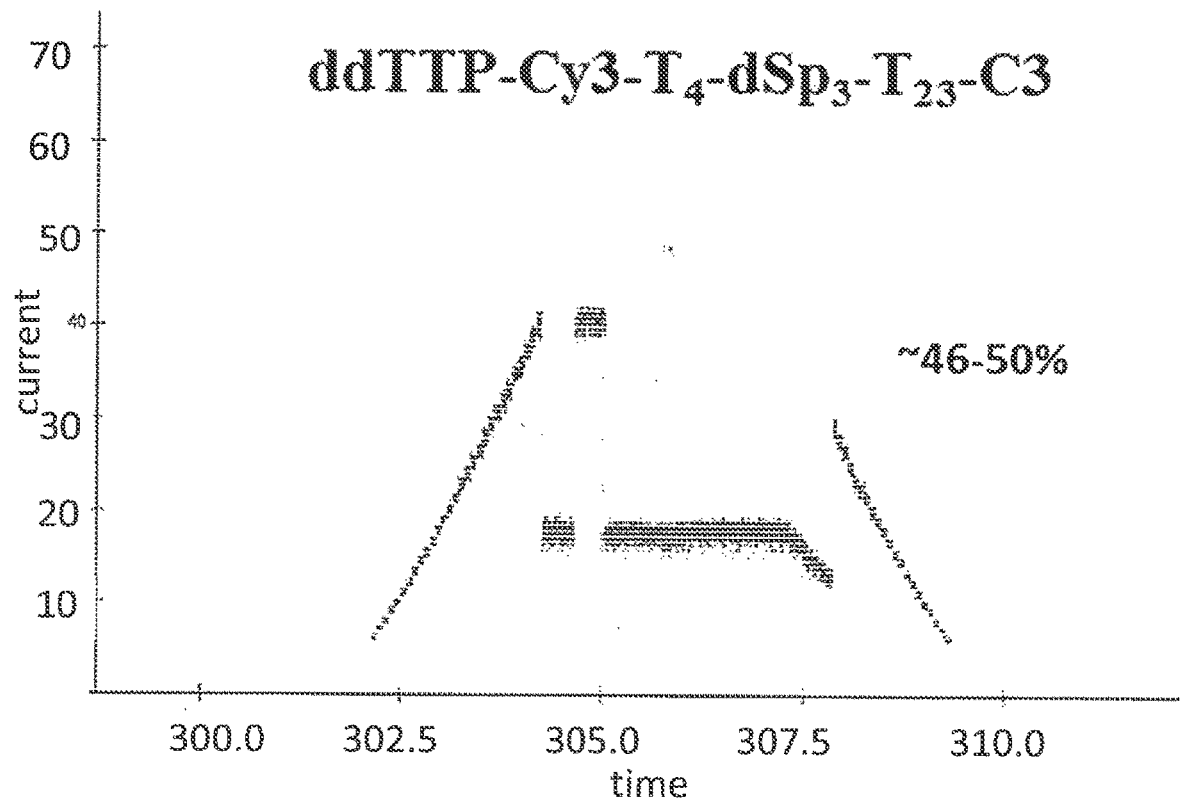

Nanopore current blockade levels generated by the tags on the primer extension products by incorporating tagged ddCTP (ddCTP-Cy3-$T_2$-d$Sp_8$-$T_{20}$-C3) and tagged ddTTP (ddTTP-Cy3-$T_4$-d$Sp_3$-$T_{23}$-C3) are shown in FIG. 10. The tag on the primer extension product incorporating a tagged ddCTP displayed a current blockade of about 26-30% of the open pore current level and the tag on the primer extension product incorporating a tagged ddTTP gave a 46-50% blockade.

Experiment 2

Conjugation of Primers to αHL Monomers

Figure 11:
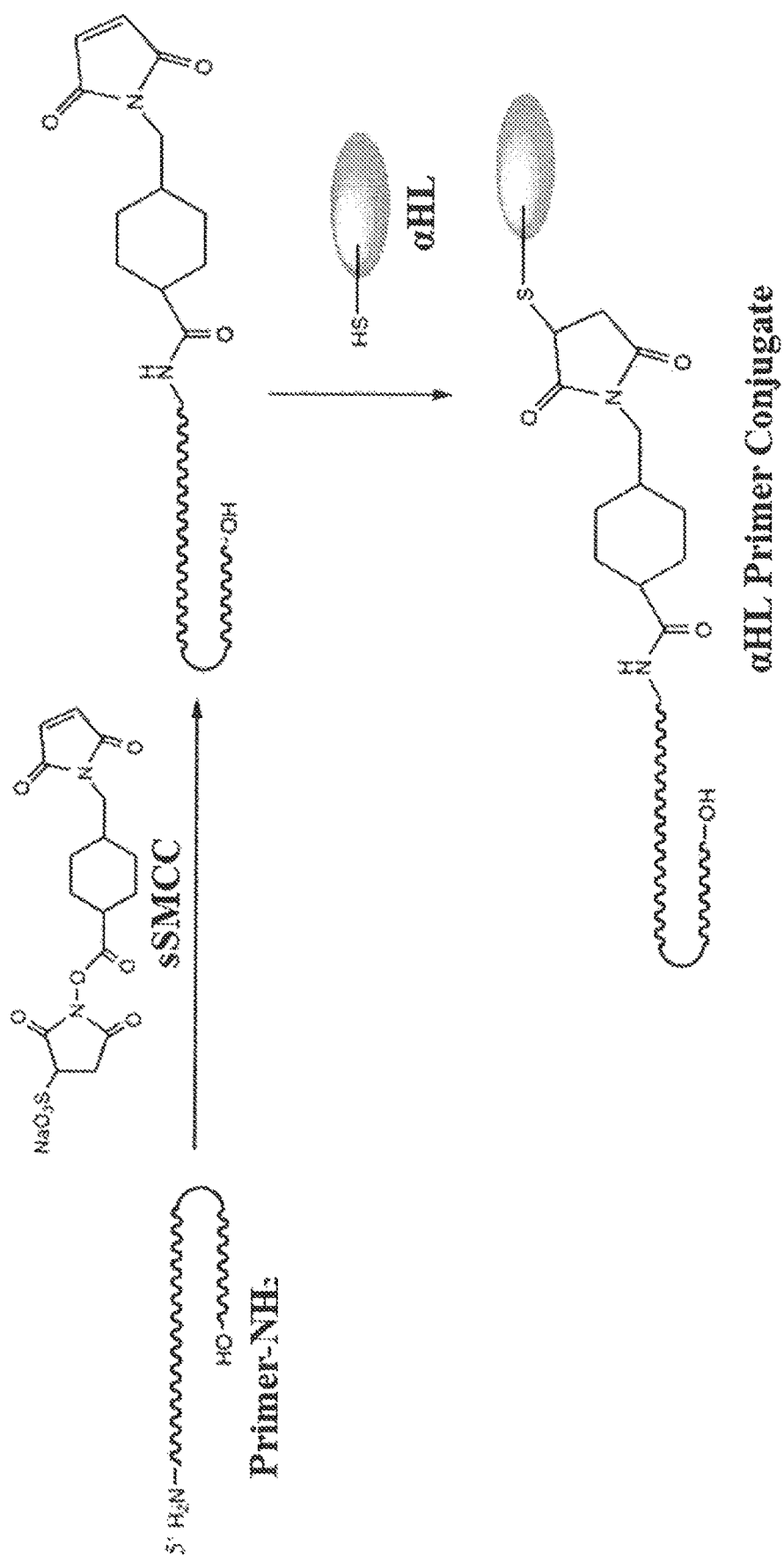
FIG. 11. Synthesis of primer-conjugated αHL. A primer with a terminal amino group is conjugated to sulfosuccinimidyl-4-(N-maleimidomethyl) cyclohexane-1-carboxylate (sSMCC) hetero bifunctional crosslinker which contains an amino-reactive N-hydroxysuccinimide (NHS ester) and a thiol-reactive maleimide group at opposite ends. The crosslinker-attached primer is then reacted with an αHL mutant having a cysteine residue at position 46, so that the maleimide group in the crosslinker reacts with the thiol group in the cysteine residue. Primary structure of recombinant hemolysin mutant 46C.

By conjugating a primer to monomeric αHL, allele discrimination and allele detection can be performed in the same environment. In order to conjugate a primer to the αHL, an engineered αHL construct, in which a lysine residue is mutated to a cysteine at position 46 (a C46 mutation) for site-specific labeling of the protein and a hexahistidine tag is added at the C-terminus, is employed for the primer attachment. Using this recombinant DNA construct, first, the C46 monomer is expressed in *Escherichia coli* strain BL21 (DE3) and purified by nickel affinity chromatography. In a separate reaction, the primer with a terminal amino group is conjugated to a sulfosuccinimidyl-4-(N-maleimidomethyl) cyclohexane-1-carboxylate (sSMCC) hetero bifunctional crosslinker which contains an amino-reactive N-hydroxysuccinimide (NHS ester) and a thiol-reactive maleimide group at opposite ends. Then, the sSMCC crosslinker-conjugated primers are purified from the residual unreacted crosslinkers in the solution by Sephadex G50. Finally, the C46 monomer is reacted with the linker-attached primers via the thiol group. This generates single primer-conjugated C46 monomers via the reaction between the thiol group in the cysteine residue in the mutant monomer and the maleimide group in the crosslinker. This scheme is shown in FIG. 11.

Experiment 3

Confirmation of Electronic Signatures

As described hereinabove, four distinct ionic current blockade patterns have been shown to be produced by the four distinct $PEG_n$ labels (n=16, 20, 24, 36) in an αHL channel at the single molecule level for DNA sequencing (Kumar et al. 2012). First, in order to confirm the above results and establish a control electronic signature for each PEG label, synthetic versions of the expected released tags (coumarin-PEGa-$NH_2$) are analyzed for their nanopore current blockade effects in a nanopore. Initially, 1M KCl is introduced to the system. Then, 1,2-diphytanoyl-sn-glycero-3-phosphocholine is added to form a lipid bilayer. Once the membrane seals the orifice, the wild type αHL monomer is injected into the solution immediately adjacent to the membrane and an electrical potential is applied to the system. The ionic current is monitored until a sudden increase in current amplitude occurs indicating formation of a single channel in the membrane. After confirming the correct current signature for the single heptameric channel insertion, coumarin-$PEG_n$-$NH_2$ molecules are added to the pores and the ionic current is recorded. From this experiment, the blockade depth and residence time distributions of each $PEG_n$ molecule over a wide range of transmembrane potentials are analyzed and conditions such as salt concentration or temperature-voltage profile are optimized for the highest signal intensities and lowest background noise. This generates the reference current signatures for the different repeat unit PEG molecules. Nucleotides labeled by tags based on modified oligonucleotides have been shown to display distinct electronic signatures in nanopores (Fuller et al. 2015).

Experiment 4

Perform Single Molecule Electronic SNP Genotyping in the Primer-Conjugated Nanopore Format After establishing the reference current signatures for each tag, the single molecule electronic SNP genotyping assay described heretofore is performed. After adding about 0.2 M KCl and forming a lipid bilayer in the system, the purified primer conjugated mutant C46 αHL described hereinabove is introduced to the lipid bilayer. Once one monomer binds to the membrane, it associates with neighboring monomers in the solution to form a homoheptameric transmembrane pore. Since the monomer described hereinabove is engineered to possess a single primer, this forms a pore bearing 7 identical primers. In order to confirm the formation of such a pore, electrical potential is applied across each individual lipid bilayer in the nanopore chip system (Fuller et al. 2015). Once the current signature that indicates the insertion of the pore is confirmed, SBE is performed by adding DNA templates containing specific SNP loci, 4 different length PEG-labeled ddNPPs (with labels attached to the base of each ddNTP) and DNA polymerase to the pore. This extends the primers by a single base with one of the 4 PEG-labeled ddNTPs if the added templates have complementarity to the attached primers in the pore.

By having several identical primers on a single pore, tags are read multiple times from a single pore, increasing the reliability efficiency of event detection. Moreover, two different current signatures should be detected from a single pore if the tested template is heterozygous while only one current signature would appear in the system if the template is homozygous (FIG. 12). In order to test this, two different templates having identical sequences except at the SNP site are designed, mixed together, and tested in the system. If the two different templates bind to primers on a single pore, the primers are extended by different tag attached ddNPPs. As a result, two different current signatures are detected from a single pore.

Experiment 5

Perform Single Molecule Electronic SNP Genotyping in the Primer-Conjugated Nanopore Format with Terminal Phosphate-Labeled Nucleotides In the case where the ddNPPs or dNPPs having polymer tags attached at their terminal phosphate positions are selected as substrates for DNA polymerase extension reaction, the tags would be expected to be released along with polyphosphates as the nucleotides are incorporated into the primers. Although the passage of individual polymer molecules through nanopores has been successfully detected and demonstrated in previous studies (Kumar et al. 2012), it might still be challenging to obtain reliable current signals from each released polymer tag molecule at the single molecule level due to their rapid translocation. In order to overcome this potential issue and ensure sufficient dwell time of the tags in the nanopore system, a high concentration of non-catalytic metal ions (Vander Horn et al. 2014) such as $Sr^{2+}$ or $Ca^2$, which permit transient binding of a complementary nucleotide to DNA polymerase but inhibit incorporation of the bound nucleotide, is added. Competing for the magnesium ($Mg^{2+}$) that catalyzes complete incorporation of ddNPPs or dNPPs to the primers, the addition of $Sr^{2+}$ or $Ca^{2+}$ extends the time between binding of the nucleotide in the polymerase closed ternary complex and release of the polyphosphate. This extended period of time allows the polymer tags to be captured and held longer in the pore while the nucleotide is still interacting with the closed form of DNA polymerase but not yet fully incorporated. Also, the rate of nucleotide incorporation by DNA polymerases in vitro can be tuned to about 100 milliseconds per base addition while the translocation of the polymer tags through the nanopore happens in microseconds. Thus, trapping the polymer tags from the nucleotides in the pore long enough to generate signals allows more accurate and reliable genotyping detection than by just letting the released polymer tags pass through the pore.

In the case where the nucleotides having polymer tags attached to the base position are chosen as substrates for the extension, there is no need to add $Sr^{2+}$ since the polymer tags are permanently incorporated in the primers that are conjugated to the pores. Thus, the long polymer tag is stably captured from the extended primer in each pore after the SBE step.

REFERENCES

Bai, R. K. & Wong, L. J. Detection and quantification of heteroplasmic mutant mitochondrial DNA by real-time amplification refractory mutation system quantitative PCR analysis: a single-step approach. *Clin. Chem.* 50, 996-1001 (2004).

Bardelli, A. et al. Mutational analysis of the tyrosine kinome in colorectal cancers. *Science* 300, 949 (2003).

Bentley, D. R. et al. Accurate whole human genome sequencing using reversible terminator chemistry. *Nature* 456, 53-59 (2008).

Bezrukov, S. M. et al. Dynamics and free energy of polymers partitioning into a nanoscale pore. *Macromolecules* 29, 8517-22 (1996).

Cerezo, M. et al. Applications of MALDI-TOF MS to large-scale human mtDNA population-based studies. *Electrophoresis* 30, 3665-3673 (2009).

Chen, X. et al. Fluorescence polarization in homogeneous nucleic acid analysis. *Genome Res.* 9: 492-498 (1999).

Cherf, G. M. et al. Automated forward and reverse ratcheting of DNA in a nanopore at 5-Å precision. *Nat. Biotechnol.* 30, 344-348 (2012).

Chowdhury, J. et al. Microfluidic Platform for Single Nucleotide Polymorphism Genotyping of the Thiopurine S-Methyltransferase Gene to Evaluate Risk for Adverse Drug Events. *J. Mol. Diagn.* 9, 521-529 (2007).

Clarke, J. et al. Continuous base identification for single-molecule nanopore DNA sequencing. *Nat. Nanotechnol.* 4, 265-70 (2009).

Ding, C. & Cantor, C. R. A high-throughput gene expression analysis technique using competitive PCR and matrix-assisted laser desorption ionization time-of-flight MS *Proc. Natl. Acad. Sci. USA*, 100, 3059-3064 (2003).

Ding, C. & Cantor, C. R. Direct molecular haplotyping of long-range genomic DNA with M1-PCR. MS *Proc. Natl. Acad. Sci. USA*, 100, 7449-7453 (2003).

Dressman, D. et al. Transforming single DNA molecules into fluorescent magnetic particles for detection and enumeration of genetic variation. *Proc. Natl. Acad. USA* 100, 8817-8822 (2003).

Duthie R. S. et al. Novel Cyanine Dye-Labeled Dideoxynucleoside Triphosphates for DNA Sequencing. *Bioconjugate Chemistry* 13, 699-706 (2002).

Eid, J. et al. Real-Time DNA Sequencing from Single Polymerase Molecules. *Science* 323, 133-138 (2009).

Fei, Z. et al. MALDI-TOF mass spectrometric typing of single nucleotide polymorphisms with mass-tagged ddNTPs. *Nucleic Acids Res.*, 26, 2827-2828 (1998).

Frazer, K. A. et al. A second generation human haplotype map of over 3.1 million SNPs. *Nature* 449, 851-861 (2007).

Fuller, C. W. et al., Chemical methods for producing tagged nucleotides. U.S Patent Application 20150368710 (2015).

Goyal, P et al., Structural and mechanistic insights into the bacterial amyloid secretion channel CsgG. *Nature* 516, 250-253 (2014).

Griffin, T. J. et al. Direct genetic analysis by matrix-assisted laser desorption/ionization mass spectrometry. *Proc. Natl. Acad. Sci. USA* 96, 6301-6306 (1999).

Griffin, T. J. & Smith, L. M. Single-nucleotide polymorphism analysis by MALDI-TOF mass spectrometry. *Trends. Biotechnol.* 18, 77-84 (2000).

Haff, L. A. & Smirnov, I. P. Multiplex genotyping of PCR products with mass tag-labeled primers. *Nucleic Acids Res.*, 25, 3749-3750 (1997).

Hardenbol, P. et al. Multiplexed genotyping with sequence-tagged molecular inversion probes. *Nat. Biotechnol.* 21: 673-678 (2003).

Harris, T. D. et al. Single-Molecule DNA Sequencing of a Viral Genome. *Science* 320, 106-109 (2008).

Hartmann, A. et al. Validation of microarray-based resequencing of 93 worldwide mitochondrial genomes. *Hum. Mutat.* 30, 115-122 (2009).

Hermanson G. T. Bioconjugate Techniques, ISBN-13: 978-0123705013 (2008).

Hobbs, F. W. & Cocuzza, A. J., Alkynylamino-nucleotides. U.S. Pat. No. 5,047,519 (1991).

Hollstein, M. et al. p53 mutations in human cancers. *Science.* 253, 49-53 (1991).

Ju, J. et al. Energy transfer fluorescent dye-labeled primers for DNA sequencing and analysis. *Proc. Natl. Acad. Sci. USA* 92, 4347-4351 (1995).

Ju, J. et al. Cassette labeling for facile construction of energy transfer fluorescent primers. *Nucleic Acids Res.* 24, 1144-1148 (1996).

Ju, J. et al. Four-Color DNA Sequencing by Synthesis Using Cleavable Fluorescent Nucleotide Reversible Terminators. *Proc. Natl. Acad. Sci. USA* 103, 19635-19640 (2006).

Kasianowicz, J. J. & Bezrukov, S. M. Protonation dynamics of the alpha-toxin ion channel from spectral analysis of pH-dependent current fluctuations. *Biophys. J.* 69, 94-105 (1995).

Kasianowicz, J. J. et al. Characterization of individual polynucleotide molecules using a membrane channel. *Proc Natl Acad Sci USA* 93, 13770-13773 (1996).

Kasianowicz, J. J. et al. Physics of DNA threading through a nanometer pore and applications to simultaneous multianalyte sensing. In *Structure and Dynamics of Confined Polymers*, ed. Kasianowicz, J. J., Kellemayer, M. S. Z. & Deamer, D. W., NATO Science Series, Kluwer Academic Publishers, The Netherlands 87, 141-164 (2002).

Kasianowicz, J. J. et al. Nanoscopic porous sensors. *Annu Rev Anal Chem* 1, 737-766 (2008).

Kheterpal, I. et al. DNA Sequencing Using a Four-Color Confocal Fluorescence Capillary Array Scanner. *Electrophoresis* 17, 1852-1859 (1996).

Kim, S. et al. Solid phase capturable dideoxynucleotides for multiplex genotyping using mass spectrometry. *Nucleic Acids Res.* 30, e85 (p 1-6) (2002).

Kim, S. et al. Multiplex Genotyping of the Human β2-Adrenergic Receptor Gene Using Solid Phase Capturable Dideoxynucleotides and Mass Spectrometry. *Analytical Biochemistry* 316, 251-258 (2003).

Kim, S. et al. Thirtyfold multiplex genotyping of the p53 gene using solid phase capturable dideoxynucleotides and mass spectrometry. *Genomics* 83, 924-931 (2004).

Krasilnikov, O. V. Sizing channels with neutral polymers. In *Structure and Dynamics of Confined Polymers*, ed. Kasianowicz, J. J., Kellemayer, M. S. Z. & Deamer, D. W. NATO Science Series, Kluwer Academic Publishers, The Netherlands 87, 97-116 (2002).

Kumar, S. et al. PEG-labeled nucleotides and nanopore detection for single molecule DNA sequencing by synthesis. *Sci Rep.* 2, 684, 1-8 (2012).

Kwok, P. Y. High-throughput genotyping assay approaches. *Pharmacogenomics* 1, 95-100 (2000).

Lander, E. S. et al. Initial sequencing and analysis of the human genome. *Nature* 409, 860-921 (2001).

Lyamichev, V. et al. Polymorphism identification and quantitative detection of genomic DNA by invasive cleavage of oligonucleotide probes. *Nat. Biotechnol.* 17, 292-296 (1999).

Manrao, E. A. et al. Reading DNA at single-nucleotide resolution with a mutant MspA nanopore and phi29 DNA polymerase. *Nat. Biotechnol.* 30, 349-353 (2012).

Margulies, M. et al. Genome sequencing in microfabricated high-density picolitre reactors. *Nature* 437, 376-380 (2005).

Misra, A. et al. Multiplex genotyping of cytochrome p450 single-nucleotide polymorphisms by use of MALDI-TOF mass spectrometry. *Clin. Chem.* 53, 933-939 (2007).

Qiu, C. et al. Design and synthesis of cleavable biotinylated dideoxynucleotides for DNA sequencing by matrix-assisted laser desorption/ionization time-of-flight mass spectrometry. *Anal. Biochem.* 427, 193-201 (2012).

Qiu, C. et al. Mitochondrial single nucleotide polymorphism genotyping by matrix-assisted laser desorption/ionization time-of-flight mass spectrometry using cleavable biotinylated dideoxynucleotides. *Anal. Biochem.* 427, 202-210 (2012).

Reiner, J. E. et al. Theory for polymer analysis using nanopore-based single-molecule mass spectrometry. *Proc Natl Acad Sci USA* 107, 12080-12085 (2010).

Robertson, J. W. et al. Single-molecule mass spectrometry in solution using a solitary nanopore. *Proc Natl Acad Sci USA* 104, 8207-11 (2007).

Rodi, C. P. et al. A strategy for the rapid discovery of disease markers using the MassARRAY™ system. *Biotechniques Suppl.* 32, S62-S69 (2002).

Roses, A. Pharmacogenetics and the practice of medicine. *Nature* 405, 857-865 (2000).

Roskey, M. T. et al. DNA sequencing by delayed extraction-matrix-assisted laser desorption/ionization time of flight mass spectrometry. *Proc. Natl. Acad. Sci. USA.* 93, 4724-4729 (1996).

Ross, P. L. et al. Discrimination of single-nucleotide polymorphisms in human DNA using peptide nucleic acid probes detected by MALDI-TOF mass spectrometry. *Anal. Chem.*, 69, 4197-4202 (1997).

Ross, P. et al. High level multiplex genotyping by MALDI-TOF mass spectrometry. *Nat. Biotechnol.* 16, 1347-1351 (1998).

Rothberg, J. M. et al. An integrated semiconductor device enabling non-optical genome sequencing. *Nature* 475, 348-352 (2011).

Salas-Solano, O. et al. Routine DNA sequencing of 1000 bases in less than one hour by capillary electrophoresis with replaceable linear polyacrylamide solutions. *Anal Chem.* 70, 3996-4003 (1998).

Smith, L. M. et al. Fluorescence detection in automated DNA sequencing analysis. *Nature,* 321, 674-679 (1986).

Song, L. et al. Structure of Staphylococcal alpha-hemolysin, a heptameric transmembrane pore. *Science* 274, 1859-1866 (1996).

Stoerker, J. et al. Rapid genotyping by MALDI-monitored nuclease selection from probe libraries. *Nat. Biotechnol.* 18, 1213-1216 (2000).

Tang, K. et al. Chip-based genotyping by mass spectrometry. *Proc. Natl. Acad. Sci. USA* 96, 10016-10020 (1999).

Tong, A. K. et al. Combinatorial Fluorescence Energy Transfer Tags for Multiplex Biological Assays. *Nat. Biotechnol.* 19, 756-759 (2001).

Tong, A. K. & Ju, J. Single-nucleotide Polymorphism Detection by Combinatorial Fluorescence Energy Transfer Tags and Biotinylated Dideoxynucleotides. *Nucleic Acids Research* 30, e19 (p1-7) (2002).

Vander Horn et al., "Nucleotide Transient Binding For Sequencing Methods" U.S. Pat. No. 8,632,975, issued Jan. 21, 2014.

Venter, J. C. et al. The sequence of the human genome. *Science* 291, 1304-1351 (2001).

Wheeler, D. A. et al. The complete genome of an individual by massively parallel DNA sequencing. *Nature* 452, 872-876 (2008).

Xiu-Cheng, F. A. et al. A rapid and accurate approach to identify single nucleotide polymorphisms of mitochondrial DNA using MALDI-TOF mass spectrometry. *Clin. Chem. Lab. Med.* 46, 299-305 (2008).

What is claimed is:

1. A method for identifying a single nucleotide residue of interest at a position within a stretch of consecutive nucleotide residues in a nucleic acid, comprising the steps of:
    a) incubating a plurality of the nucleic acids, under an applied voltage, with
        (1) a nanopore, wherein the nanopore is conjugated to identical primers, and wherein the nanopore comprises:
            i) seven alpha hemolysin monomers; or
            ii) eight MspA monomers; or
            iii) nine CsgG monomers;
                wherein one of the identical primers is hybridized to the nucleotides in a nucleic acid of the plurality of nucleic acids immediately 3' to the single nucleotide residue of interest;
        (2) at least one labeled terminating nucleotide polyphosphate (NPP) analogue,
            wherein the at least one NPP analogue has the structure:

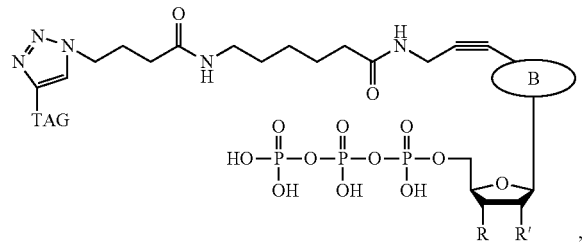

wherein B is a base selected from the group consisting of adenine, cytosine, thymine, uracil, guanine, 7-deaza-adenine, 7-deaza-guanine and analogs thereof;
        R and R' are each independently H, OH, O-alkyl, F, Cl, Br, $N_3$, $NH_2$, O—$NH_2$, O-allyl, O—$CH_2N_3$, 2', 3'-isopropylidine or groups which only allow a single nucleotide to be incorporated by DNA polymerase; and
        TAG comprises any polymeric molecule that can be detected by the nanopore; and
        (3) a nucleic acid polymerase;
            so that an NPP analogue is incorporated into the primer if it is complementary to the single nucleotide residue of interest, and the label attached to the incorporated NPP analogue is drawn into the nanopore;
    b) detecting by nanopore the signature of the label of the NPP analogue incorporated into the primer, so as to identify the incorporated NPP analogue;
    thereby identifying the single nucleotide residue of interest.

2. The method of claim 1, wherein the nucleic acid is incubated with one NPP analogue, and if the NPP analogue is not incorporated, iteratively repeating the incubating with a different NPP analogue until an NPP analogue is incorporated and its label detected by nanopore.

3. The method of claim 1, wherein the at least one NPP analogue is a dideoxyribonucleotide polyphosphate (ddNPP).

4. The method of claim 3, wherein the label comprises one or more of ethylene glycol, an amino acid, a carbohydrate, a peptide, a dye, a chemiluminescent compound, a mononucleotide, a dinucleotide, a trinucleotide, a tetranucleotide, a pentanucleotide, a hexanucleotide, an oligonucleotide, an aliphatic acid, an aromatic acid, an alcohol, a thiol group, a cyano group, a nitro group, an alkyl group, an alkenyl group, an alkynyl group, an azido group, or a combination thereof.

5. The method of claim 4, wherein in step a)(2) the nucleic acid is incubated with four coumarin-PEG-ddNPPs, each comprising a different base, and each comprising a coumarin-PEG-label of a different length.

6. The method of claim 4, wherein the nucleic acid is incubated with four oligonucleotide-tagged ddNPPs, each comprising a different base, and each comprising an oligonucleotide of different length and/or composition.

7. The method of claim 6, wherein the oligonucleotides comprise 10-50 monomeric units.

8. The method of claim 1, wherein TAG is selected from the group consisting of:
    i) oligonucleotides;
    ii) peptides;
    iii) carbohydrates; and
    iv) PEGs of different lengths.

9. The method of claim 1, wherein in step a) (1) the nanopore comprises seven alpha hemolysin monomers, wherein the lysine residue of each monomer is mutated to a cysteine at position 46.

10. A method for identifying a single nucleotide residue of interest at a position within a stretch of consecutive nucleotide residues in a nucleic acid, comprising the steps of:
    (a) incubating a plurality of the nucleic acids, under an applied voltage, with
        (1) a nanopore, wherein the nanopore is conjugated to identical primers, and wherein the nanopore comprises:
            i) seven alpha hemolysin monomers; or
            ii) eight MspA monomers; or
            iii) nine CsgG monomers;
                wherein one of the identical primers is hybridized to the nucleotides in a nucleic acid of the plurality of nucleic acids immediately 3' to the single nucleotide residue of interest;
        (2) at least one labeled nucleotide polyphosphate (NPP) analogue,
            wherein the at least one NPP analogue has the structure:

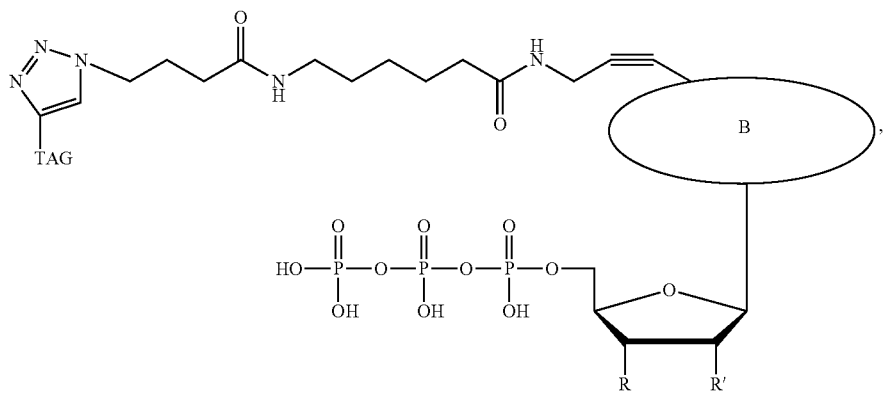

wherein B is a base selected from the group consisting of adenine, cytosine, thymine, uracil, guanine, 7-deaza-adenine, 7-deaza-guanine and analogs thereof;

R and R' are each independently H, OH, O-alkyl, F, Cl, Br, $N_3$, $NH_2$, O—$NH_2$, O-allyl, O—$CH_2N_3$, 2', 3'-isopropylidine or groups which only allow a single nucleotide to be incorporated by DNA polymerase; and TAG comprises any polymeric molecule that can be detected by the nanopore; and (3) a nucleic acid polymerase; and (4) a non-catalytic ion which permits transient binding of a complementary labeled NPP analogue to the nucleic acid polymerase but inhibits incorporation of the bound NPP analogue;

so that an NPP analogue is transiently bound to the nucleic acid polymerase if it is complementary to the single nucleotide of interest, and the label attached to the transiently bound NPP analogue is drawn into the nanopore;

(b) detecting by nanopore the signature of the label of the NPP analogue transiently bound to the primed template by polymerase, so as to identify the NPP analogue;

thereby identifying the single nucleotide residue of interest.

11. The method of claim 10, wherein in step (a) the nucleic acid is incubated with one NPP analogue, and if the NPP analogue does not transiently bind to the nucleic acid polymerase, iteratively repeating the incubating with a different NPP analogue until an NPP analogue is transiently bound and its label detected by the nanopore.

12. The method of claim 10, wherein the non-catalytic metal ion is $Sr^{2+}$ or $Ca^{2+}$.

13. The method of claim 10, wherein the label comprises one or more of ethylene glycol, an amino acid, a carbohydrate, a peptide, a dye, a chemiluminescent compound, a mononucleotide, a dinucleotide, a trinucleotide, a tetranucleotide, a pentanucleotide, a hexanucleotide, an oligonucleotide, an aliphatic acid, an aromatic acid, an alcohol, a thiol group, a cyano group, a nitro group, an alkyl group, an alkenyl group, an alkynyl group, an azido group, or a combination thereof.

14. The method of claim 13, wherein in step a) (2) the nucleic acid is incubated with four coumarin-PEG-ddNPPs, each comprising a different base, and each comprising a coumarin-PEG-label of a different length.

15. The method of claim 13, wherein the nucleic acid is incubated with four oligonucleotide-tagged NPPs, each comprising a different base, and each comprising an oligonucleotide of different length and/or composition.

16. The method of claim 15, wherein the oligonucleotides comprise 10-50 monomeric units.

17. The method of claim 10, wherein TAG is selected from the group consisting of:
  i) oligonucleotides;
  ii) peptides;
  iii) carbohydrates; and
  iv) PEGs of different lengths.

18. The method of claim 10, wherein in step a) (1) the nanopore comprises seven alpha hemolysin monomers, wherein the lysine residue of each monomer is mutated to a cysteine at position 46.

* * * * *

SEQUENCE LISTING

<160> NUMBER OF SEQ ID NOS: 2

<210> SEQ ID NO 1
<211> LENGTH: 26
<212> TYPE: DNA

<210> SEQ ID NO 2
<211> LENGTH: 302
<212> TYPE: PRT
<213> ORGANISM: Artificial Sequence
<220> FEATURE:
<223> OTHER INFORMATION: template

<400> SEQUENCE: 1
gatagcgccg cgccttggcg cggcgc                                          26

<210> SEQ ID NO 2
<211> LENGTH: 302
<212> TYPE: PRT
<213> ORGANISM: Artificial Sequence
<220> FEATURE:
<223> OTHER INFORMATION: Hemolysin mutant

<400> SEQUENCE: 2

```
Met Ala Asp Ser Asp Ile Asn Ile Lys Thr Gly Thr Thr Asp Ile Gly
1               5                   10                  15

Ser Asn Thr Thr Val Lys Thr Gly Asp Leu Val Thr Tyr Asp Lys Glu
            20                  25                  30

Asn Gly Met His Lys Lys Val Phe Tyr Ser Phe Ile Asp Asp Cys Asn
        35                  40                  45

His Asn Lys Lys Leu Leu Val Ile Arg Thr Lys Gly Thr Ile Ala Gly
    50                  55                  60

Gln Tyr Arg Val Tyr Ser Glu Glu Gly Ala Asn Lys Ser Gly Leu Ala
65                  70                  75                  80

Trp Pro Ser Ala Phe Lys Val Gln Leu Gln Leu Pro Asp Asn Glu Val
                85                  90                  95

Ala Gln Ile Ser Asp Tyr Tyr Pro Arg Asn Ser Ile Asp Thr Lys Glu
            100                 105                 110

Tyr Met Ser Thr Leu Thr Tyr Gly Phe Asn Gly Asn Val Thr Gly Asp
        115                 120                 125

Asp Thr Gly Lys Ile Gly Gly Leu Ile Gly Ala Asn Val Ser Ile Gly
    130                 135                 140

His Thr Leu Lys Tyr Val Gln Pro Asp Phe Lys Thr Ile Leu Glu Ser
145                 150                 155                 160

Pro Thr Asp Lys Lys Val Gly Trp Lys Val Ile Phe Asn Asn Met Val
                165                 170                 175

Asn Gln Asn Trp Gly Pro Tyr Asp Arg Asp Ser Trp Asn Pro Val Tyr
            180                 185                 190

Gly Asn Gln Leu Phe Met Lys Thr Arg Asn Gly Ser Met Lys Ala Ala
        195                 200                 205

Glu Asn Phe Leu Asp Pro Asn Lys Ala Ser Ser Leu Leu Ser Ser Gly
    210                 215                 220

Phe Ser Pro Asp Phe Ala Thr Val Ile Thr Met Asp Arg Lys Ala Ser
225                 230                 235                 240
```

-continued

```
Lys Gln Gln Thr Asn Ile Asp Val Ile Tyr Glu Arg Val Arg Asp Asp
            245                 250                 255

Tyr Gln Leu His Trp Thr Ser Thr Asn Trp Lys Gly Thr Asn Thr Lys
            260                 265                 270

Asp Lys Trp Thr Asp Arg Ser Ser Glu Arg Tyr Lys Ile Asp Trp Glu
            275                 280                 285

Lys Glu Glu Met Thr Asn Lys Gly His His His His His
    290                 295                 300
```